(12) United States Patent
Mazess et al.

(10) Patent No.: US 6,282,261 B1
(45) Date of Patent: Aug. 28, 2001

(54) MULTI-MODE X-RAY IMAGE INTENSIFIER SYSTEM

(75) Inventors: Richard B. Mazess, Madison; David L. Ergun, Verona; Joseph P. Bisek, Madison, all of WI (US)

(73) Assignee: Lunar Corporation, Madison, WI (US)

( * ) Notice: Subject to any disclaimer, the term of this patent is extended or adjusted under 35 U.S.C. 154(b) by 0 days.

(21) Appl. No.: 09/574,937

(22) Filed: May 19, 2000

Related U.S. Application Data

(63) Continuation-in-part of application No. 09/538,093, filed on Mar. 29, 2000, which is a continuation of application No. 09/281,518, filed on Mar. 30, 1999, which is a continuation-in-part of application No. 09/006,358, filed on Jan. 13, 1998, now Pat. No. 6,007,243, which is a continuation-in-part of application No. PCT/JP97/02770, filed on Feb. 21, 1997.
(60) Provisional application No. 60/080,164, filed on Mar. 31, 1998, and provisional application No. 60/011,993, filed on Feb. 21, 1996.

(51) Int. Cl.[7] .................................................. H05G 1/64
(52) U.S. Cl. ..................... 378/98.3; 378/98.2; 378/98.8
(58) Field of Search ........................... 378/98.2, 98.3, 378/98.8

(56) References Cited

U.S. PATENT DOCUMENTS

| | | | |
|---|---|---|---|
| 4,367,490 | 1/1983 | Riederer | 358/167 |
| 4,736,399 * | 4/1988 | Okazaki | 378/98.2 |
| 4,802,197 | 1/1989 | Juergens | 378/197 |
| 4,829,549 | 5/1989 | Vogel et al. | 378/55 |
| 4,952,805 | 8/1990 | Tanaka | 250/327.2 |
| 5,012,504 | 4/1991 | McFaul et al. | 378/108 |
| 5,042,489 | 8/1991 | Wiener et al. | 128/661.03 |
| 5,150,421 | 9/1992 | Morishita et al. | 382/6 |
| 5,164,993 | 11/1992 | Capozzi et al. | 382/6 |
| 5,263,074 * | 11/1993 | Sakamoto | 378/98.2 |
| 5,319,749 * | 6/1994 | Haaker et al. | 345/511 |
| 5,336,880 | 8/1994 | Laclerc et al. | 250/214 |
| 5,388,138 | 2/1995 | Fujiwara | 378/108 |
| 5,412,705 * | 5/1995 | Snoeren et al. | 378/98.3 |
| 5,416,818 | 5/1995 | Takahashi et al. | 378/98.7 |
| 5,467,380 | 11/1995 | De Jonge et al. | 378/98.2 |
| 5,485,500 * | 1/1996 | Baba et al. | 378/98.2 |
| 5,526,442 * | 6/1996 | Baba et al. | 382/132 |
| 5,574,764 | 11/1996 | Granfors et al. | 378/98.7 |
| 5,627,873 | 5/1997 | Hanover et al. | 378/197 |
| 5,640,436 * | 6/1997 | Kawai et al. | 378/4 |
| 5,642,395 | 6/1997 | Anderton et al. | 378/198 |
| 5,712,890 * | 1/1998 | Spivey et al. | 378/37 |
| 5,771,269 | 6/1998 | Chao | 378/5 |
| 6,002,743 * | 12/1999 | Telymonde | 378/98.8 |
| 6,018,565 * | 1/2000 | Ergun et al. | 378/95 |
| 6,118,845 * | 9/2000 | Simon et al. | 378/62 |

FOREIGN PATENT DOCUMENTS

| | | |
|---|---|---|
| 0218923A2 | 9/1986 | (EP) . |
| 0283255 | 3/1988 | (EP) . |

OTHER PUBLICATIONS

K. Machin and S. Webb, Cone–Beam X–Ray Microtomography of Small Specimens, Physics in Medicine and Biology 39 (1994) Oct., No. 10, pp. 1639–1657.

* cited by examiner

*Primary Examiner*—Robert H. Kim
*Assistant Examiner*—Allen C. Ho
(74) *Attorney, Agent, or Firm*—Quarles & Brady LLP

(57) ABSTRACT

A short form intensifier is provided having a plurality of cameras each providing a portion of the image of the image intensifier to reduce the focal length and hence the distortion of each camera individually. The images may be collected to provide a single contiguous image. Multiple lenses may be associated with different correction factors in associated correction circuitry.

20 Claims, 15 Drawing Sheets

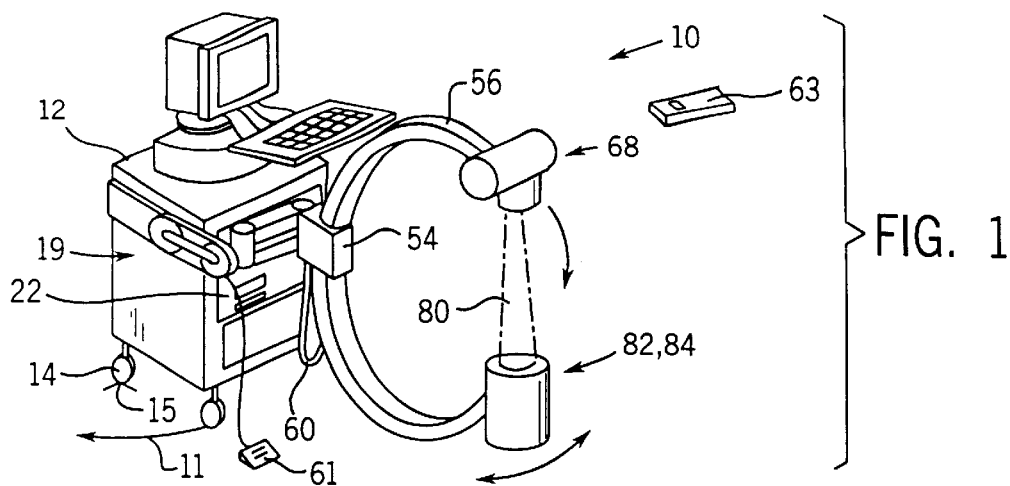
FIG. 1
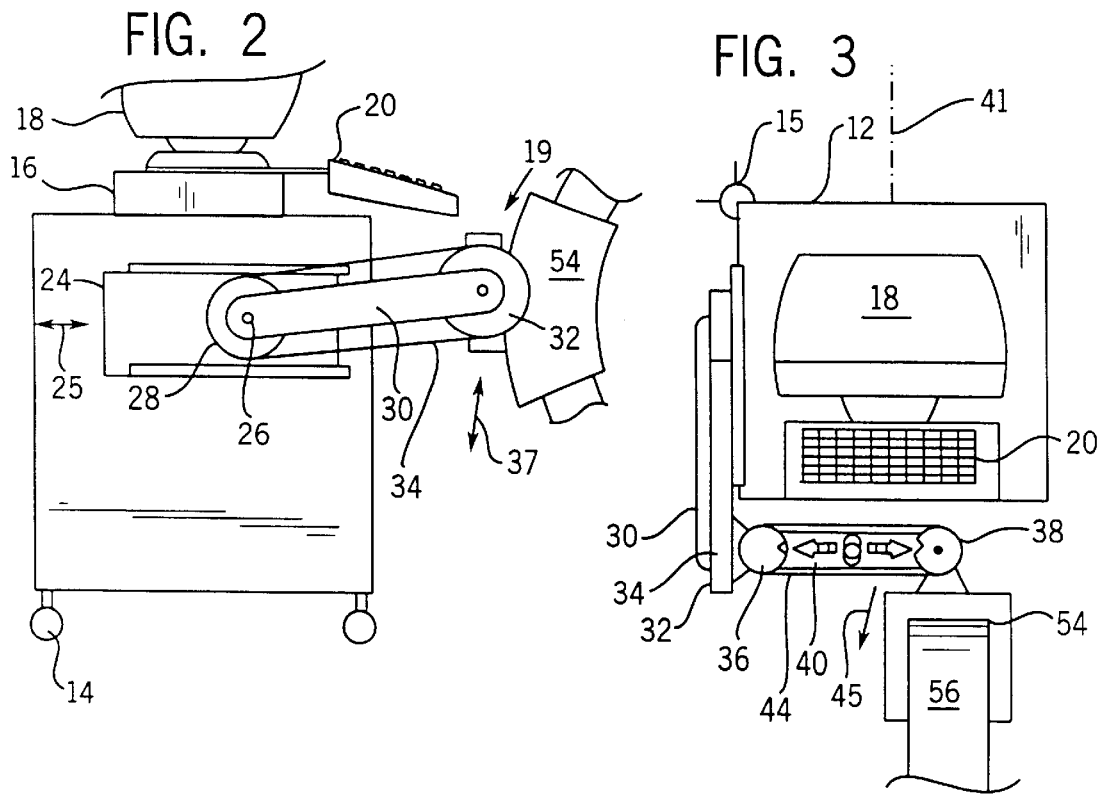
FIG. 2
FIG. 3
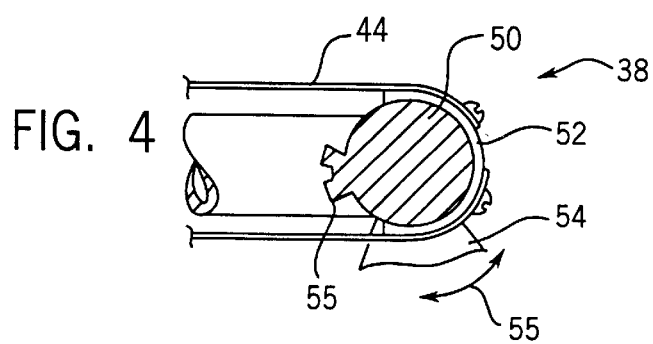
FIG. 4

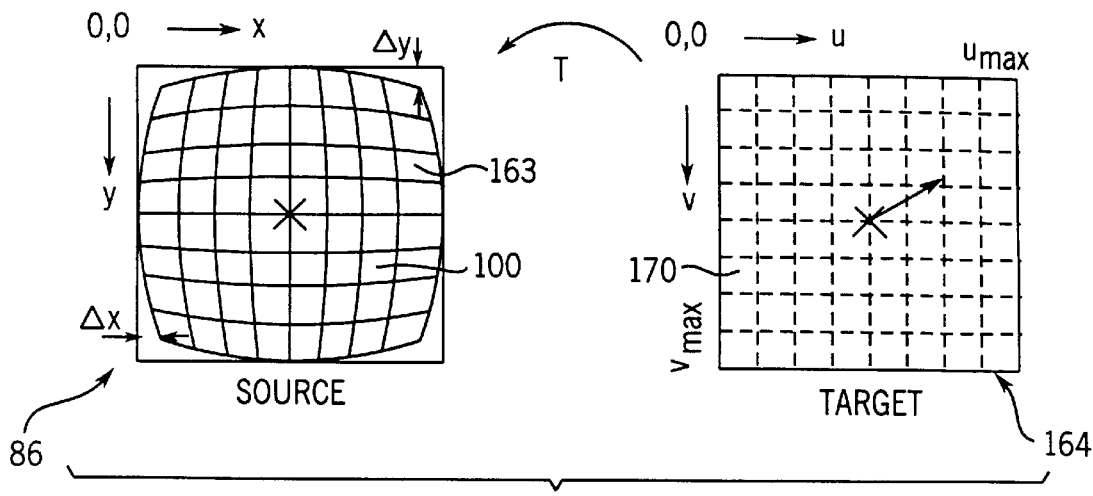
FIG. 19
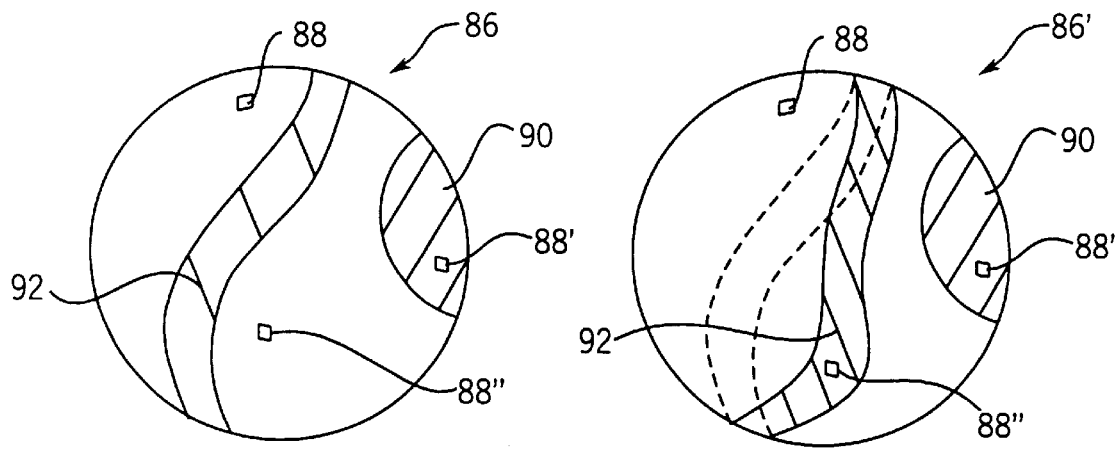
FIG. 7
FIG. 8
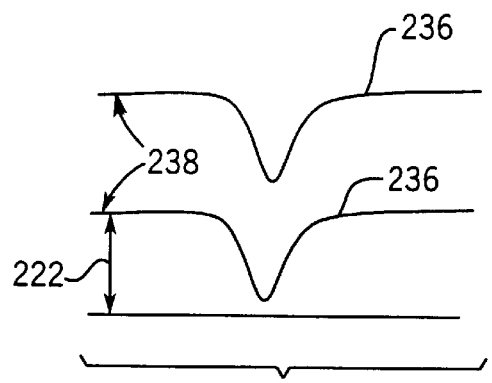
FIG. 24

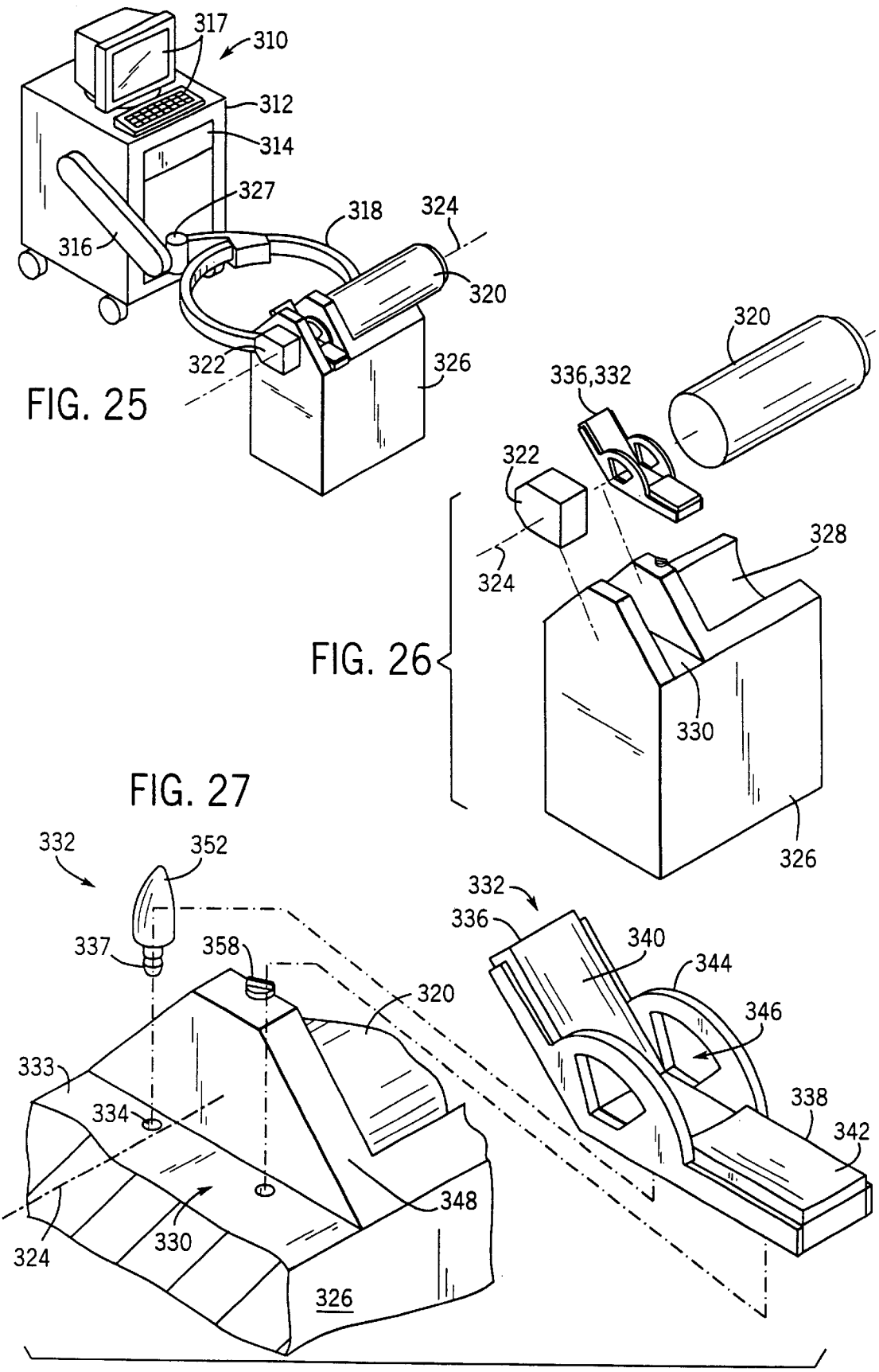

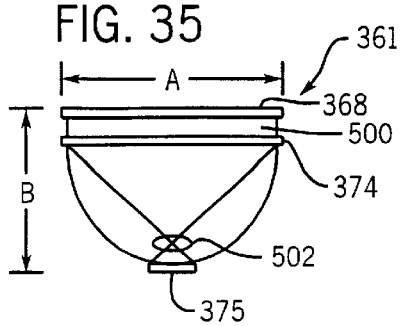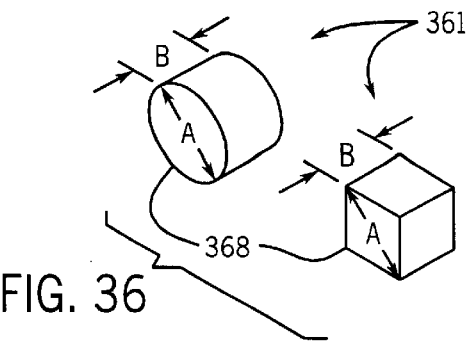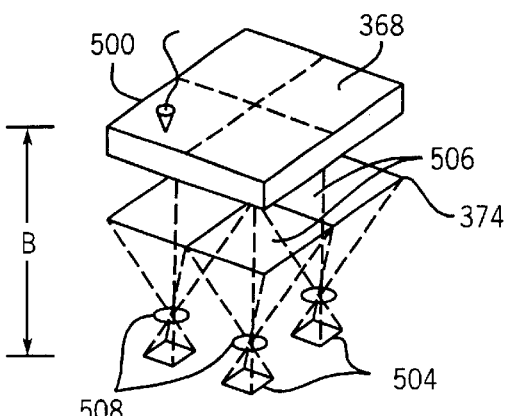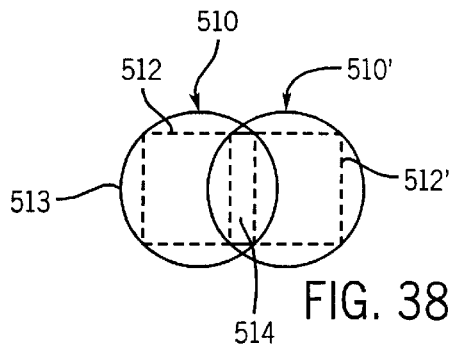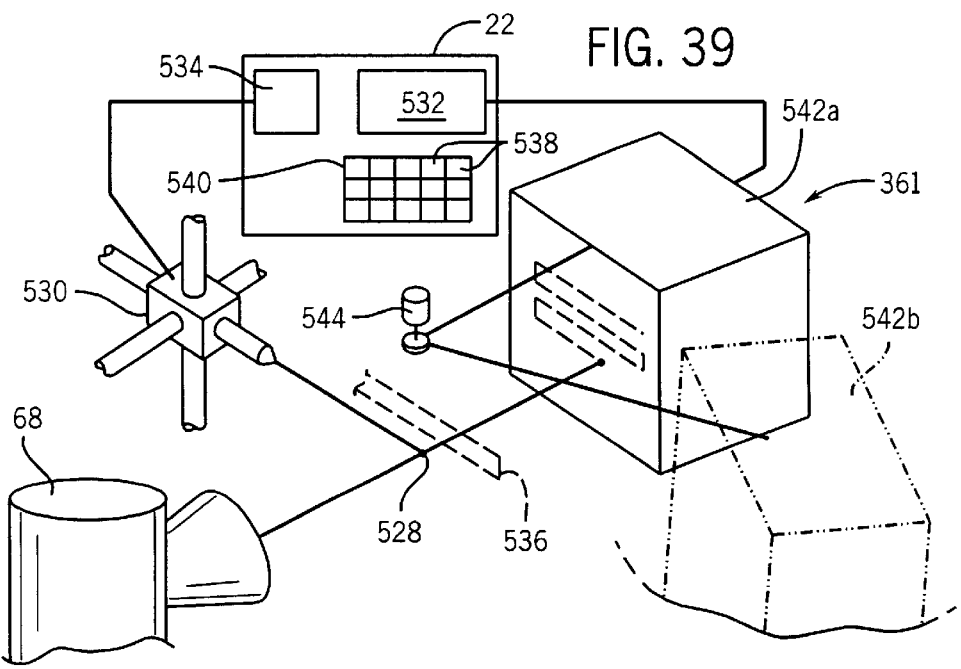

MULTI-MODE X-RAY IMAGE INTENSIFIER SYSTEM

CROSS-REFERENCE TO RELATED APPLICATIONS

This application is a CIP of application Ser. No. 09/538,093 filed Mar. 29, 2000; which is a CON of application Ser. No. 09/281,518 filed Mar. 30, 1999 which claims benefit to Ser. No. 60/080,164 filed Mar. 31, 1998; and which is a CIP of application Ser. No. 09/006,358 filed Jan. 13, 1998, now U.S. Pat. No. 6,007,243 filed Dec. 28, 1999 which is a CIP of PCT 97/02770 dated Feb. 21, 1997; which claims benefit to Ser. No. 60/011,993 filed Feb. 21, 1996.

BACKGROUND OF THE INVENTION

The present invention relates to x-ray image intensifiers allowing x-ray imaging using low intensity x-rays. In particular, the invention relates to an image intensifier having a shortened form factor.

X-ray images are produced by projecting x-rays from an x-ray source, through an object to be imaged, to an x-ray detector. In x-ray fluoroscopy, x-rays are projected semi-continuously to a phosphor panel that emits light when struck by the x-rays.

In order to reduce the x-ray dose needed to produce such an image, modern fluoroscopy machines may use an image intensifier. A conventional image intensifier tube provides a front phosphor surface receiving x-rays and converting them to light. The light exits from the rear side of the phosphor surface and strikes a photo cathode, which converts the light to electrons that are discharged into an evacuated chamber behind the photo cathode.

High voltage plates, increasing the energy of individual electrons and/or their number, amplify the electrons. Focusing electrodes, micro channel plates, or other means may be used to preserve the spatial relationship of the electrons until the time they hit a target phosphor material to produce an optical image. This latter image is substantially brighter than that formed by the front phosphor surface. An electronic camera such as those using a charge-coupled device (CCD) may record the optical image to convert the optical image to electrical signals.

A drawback to image intensifiers is that they are relatively bulky structures often having a length several times the width of the entrance aperture defined by the front phosphor surface. X-ray machines using image intensifiers guide physicians in invasive procedures, such as catheterizations. A bulky image intensifier may interfere with the required repositioning of the x-ray machine during such procedures.

It is difficult to make the image intensifier shorter for a given entrance aperture. If the path over which the electrons are focused is reduced, the spatial distortion of the electrons increases requiring more complex focusing fields and structures. At some point the distortion compromises accurate guidance of medical instruments.

Micro channel plates can be used to amplify the electron stream without focusing it to a smaller area, eliminating the distortion of the electron focusing process. The large area image produced by such a micro channel system, however, must then be optically reduced by the lens system of the electronic camera. Short focal length optical reduction introduces distortion similar to those produced by short length electron focusing.

BRIEF SUMMARY OF THE INVENTION

The present invention provides an extremely short form image intensifier with low image distortion. This is accomplished by the use of multiple cameras, each of which receive only a portion of the image generated by the image intensifier. The multiple cameras allow longer focal length lenses to be used reducing distortion of the images and possibly increasing resolution. Minor image distortion is corrected through an electronic image correction circuit prior to assembling the multiple images of the multiple cameras into a single image. Each camera may have its own correction factors.

Multiple correction factors may also allow the use of multiple lenses each having a different correction factor. As the lenses are switched into position or refocused, the appropriate correction factor may be provided to the image correction circuitry. A similar approach may be used to correct for changing image distortion caused, for example, by changing orientations of the image intensifier with respect to the earth's magnetic field.

Specifically, then, the present invention provides an imaging x-ray detector having an image intensifier, at least two digital cameras and an image correction circuit. The image intensifier includes a front target ejecting electrons into an internal volume of the image intensifier upon receipt of x-rays. An electron amplifier receives the ejected electrons to amplify the same and to direct them against a rear target receiving the amplified electrons to produce an optical image.

The digital cameras are directed toward the rear target to produce digital signals representing different portions of the optical image projected at a camera image plane. An image correction circuit receives the digital signals and corrects for spatial distortion underlying different portions of the optical image captured in the digital signals and provides corrected images to a combining circuit receiving the corrected digital signals and combining them to produce a spatially continuous representation of the optical image.

Thus it is one object of the invention to use multiple digital cameras to provide low distortion, large entrance aperture image intensifiers. The image correction circuit allows the multiple images to be seamlessly blended together.

The different portions of the optical image recorded by the cameras may include overlapping portions and the combining circuit may apply weighting values to the digital signals representing overlapping portions prior to combining the digital signals.

Thus it is another object of the invention to accommodate a degree of overlap in the camera field of views without unduly emphasizing the overlapped regions as would occur with a simple addition.

The rear target may be rectangular and the invention may provide four digital cameras directed toward different quadrants of the optical image on the rear target.

Thus it is another object of the invention to provide for a rectangular image intensifier in distinction to the normal circular image intensifier systems without excessive image distortion. The use of multiple cameras allows for the square image to be more readily generated with simple optical structures.

The front target may receive x-rays across a width and the camera plane may be removed from the target by an amount no greater than the width. The front target may be rectangular and the width may be a measure of the diagonal of the rectangle of the front target or the front target may be circular and the width may be a measure of the diameter of the front target.

Thus it is another object of the invention to provide an extremely short form factor image intensifier that is no deeper than it is wide.

In an alternative embodiment, the imaging x-ray detector may include as few as one camera and the image correction circuit may store multiple correction parameters and receive a mode signal to apply a selected one of different correction parameters to the digital signal from the camera dependent on the mode signal for correcting for spatial distortion of underlying optical images captured in the digital signals.

Thus it is another object of one aspect of the invention to provide for different spatial distortion corrections associated with different modes of operation of the detector.

The invention may include an orientation sensor for detecting an orientation of the imaging x-ray detector to produce the mode signal. Alternatively, the invention may provide a lens support positioning at least one lens between the rear target and the imaging array according to the mode signal to project the optical image onto the imaging array at different magnifications associated with the mode signals.

Thus it is another object of the invention to provide an image intensifier tube offering improved imaging flexibility in terms of orientation and magnification without compromising on image distortion.

The foregoing and other objects and advantages of the invention will appear from the following description. In this description, reference is made to the accompanying drawings, which form a part hereof, and in which there is shown by way of illustration, a preferred embodiment of the invention. Such embodiment and its particular objects and advantages do not defined the scope of the invention, however, and reference must be made therefore to the claims for interpreting the scope of the invention.

BRIEF DESCRIPTION OF THE DRAWINGS

FIG. 1 is a perspective view of the fluoroscopy machine suitable for use with the present invention showing a C-arm supporting an image intensifier/video camera and x-ray tube in opposition for rotation in a vertical plane, the C-arm held along a mid-line of a cart by an articulated arm attached to the side of the cart;

FIG. 2 is a side view in elevation of the cart of FIG. 1 showing a slide attaching the articulated arm, to the side of the cart and showing a four-bar linkage motion of the arm for elevation of the C-arm;

FIG. 3 is a top view of the C-arm system of FIG. 1 with the articulated arm in partial phantom showing the four-bar linkage of the arm for extending the C-arm toward and away from the cart;

FIG. 4 is a detail fragmentary view of an outer pivot of the articulated arm attached to the C-arm such as allows limited pivoting of a plane of rotation of the C-arm about a vertical axis;

FIGS. 7 and 8 are simplified images such as may be obtained by the system of FIG. 1 showing portions of the image having moving elements and portions having stationary elements;

FIG. 19 is a schematic representation of a distorted image of FIG. 11 and a schematic representation of a corresponding undistorted image showing the variables used in the mathematical transformation of the distorted image to correct for rotation and distortion;

FIG. 24 is a graphical representation of an adjustment of calculated scatter from the image of FIG. 23 based on normalizing points established by the occluder of FIG. 21;

FIG. 25 is a perspective view similar to that of FIG. 1 showing a C-arm system similar to that of FIG. 1 in position on the densitometry cradle of the present invention to provide a beam of x-rays along a horizontal axis across the top of the cradle;

FIG. 26 is a fragmentary exploded view of the x-ray detector and x-ray source of the C-arm system of FIG. 25 removed from the cradle and showing a removable foot positioner also removed from the cradle;

Figure 6:
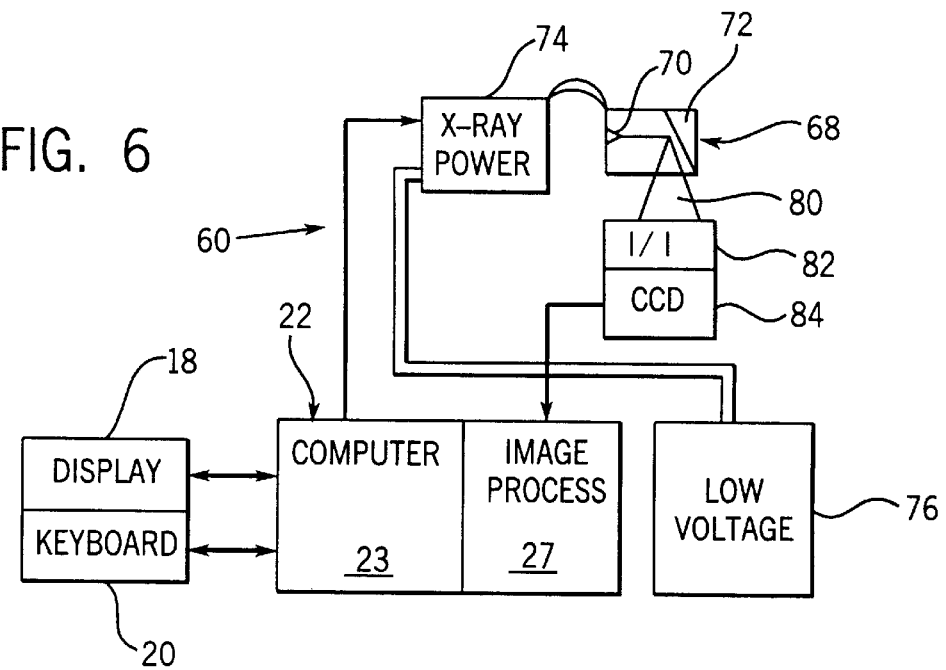
FIG. 6 is a schematic block diagram of the fluoroscopy machine of FIG. 1 showing the path of control of a remote x-ray tube power supply by a microprocessor and the receipt of data from the image intensifier/video camera by the microprocessor for image processing.
Figure 28:
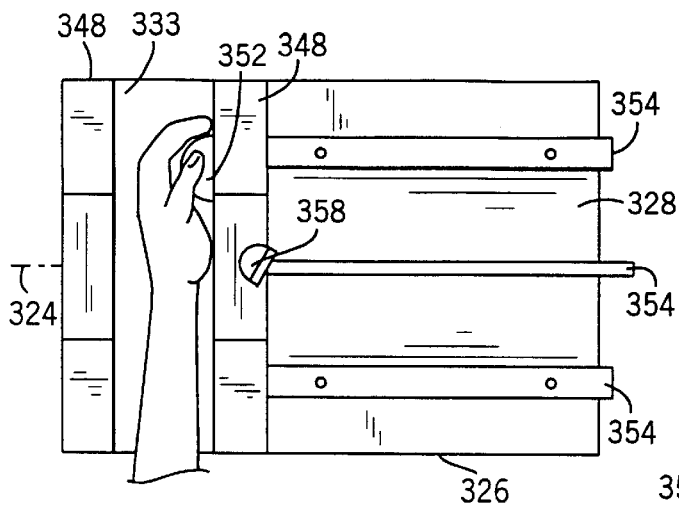
Figure 29:
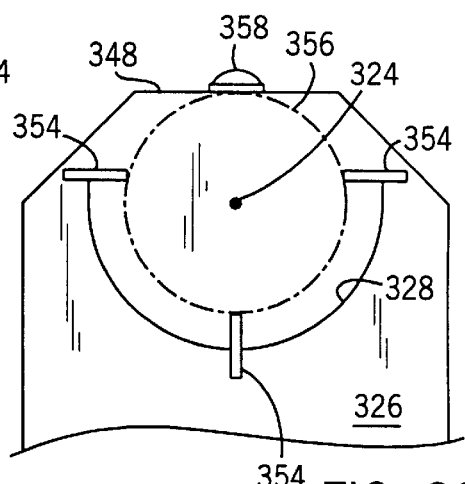
Figure 30:
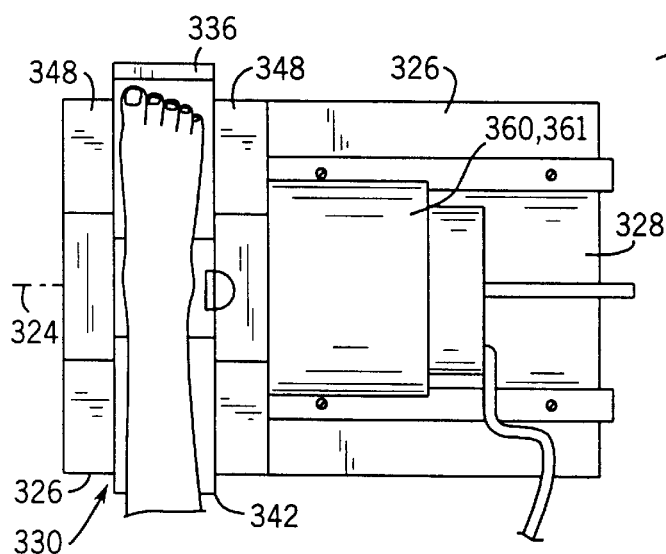
Figure 31:
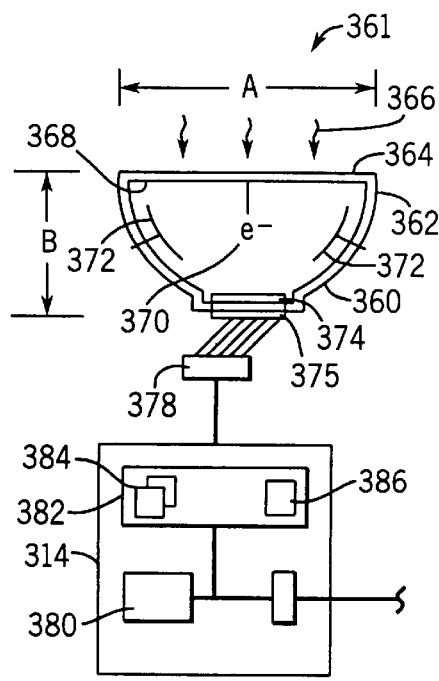
Figure 32:
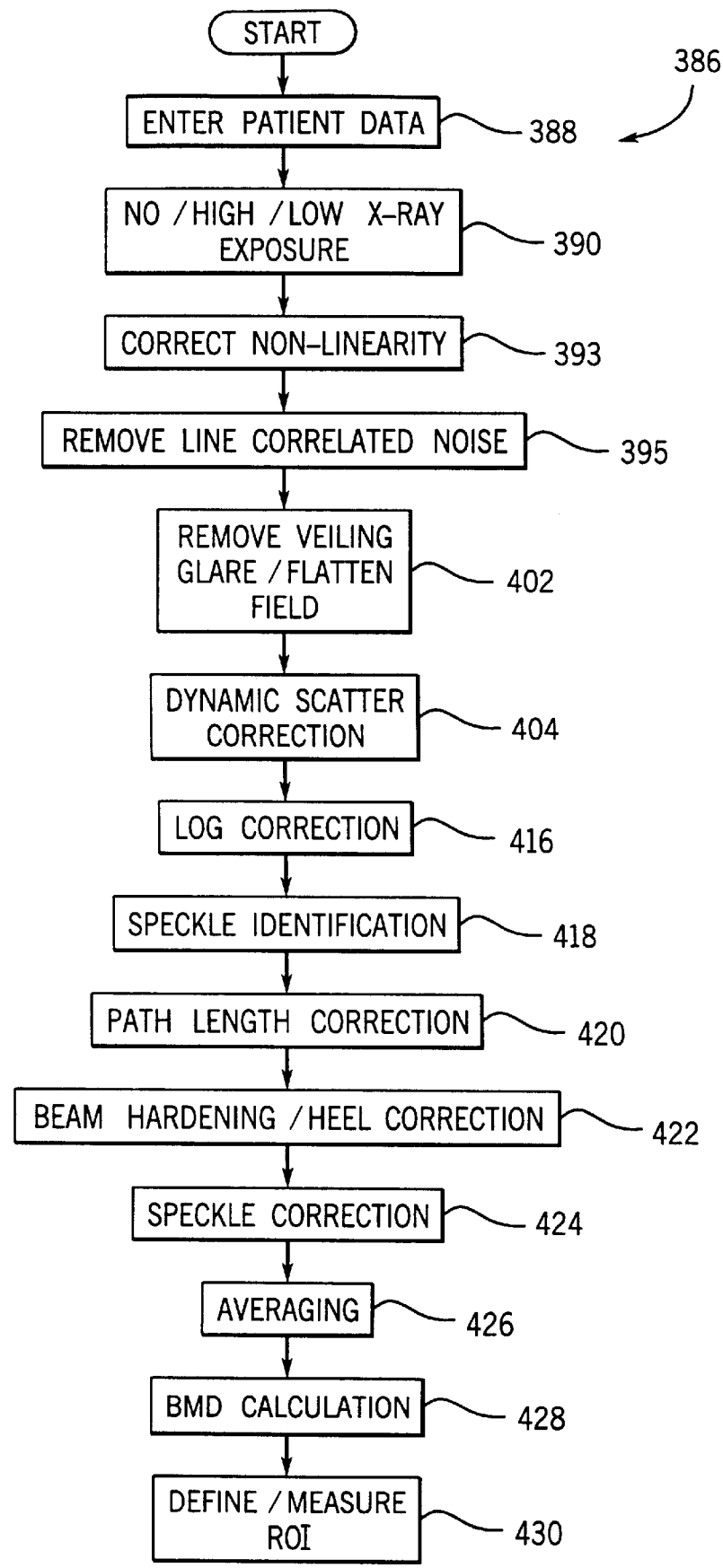
Figure 33:
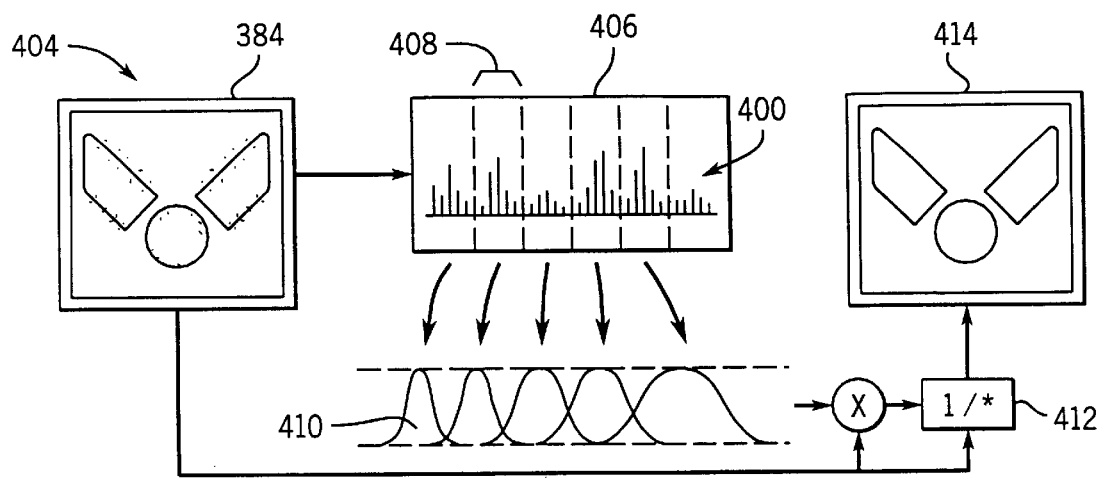
Figure 34:
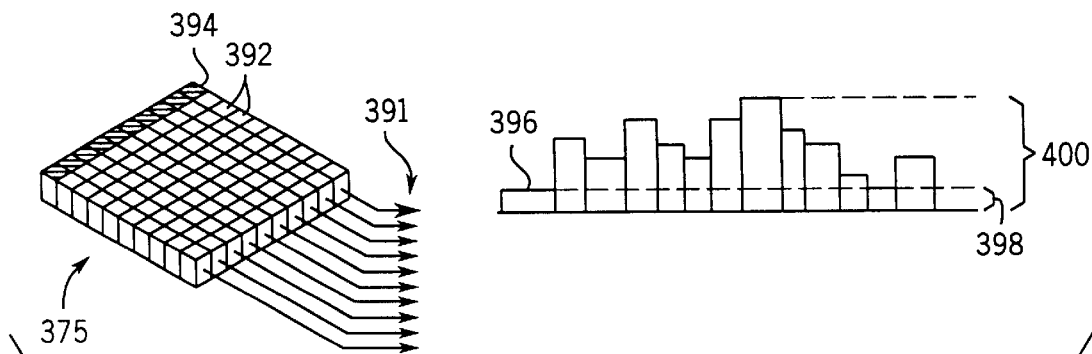
Figure 40:
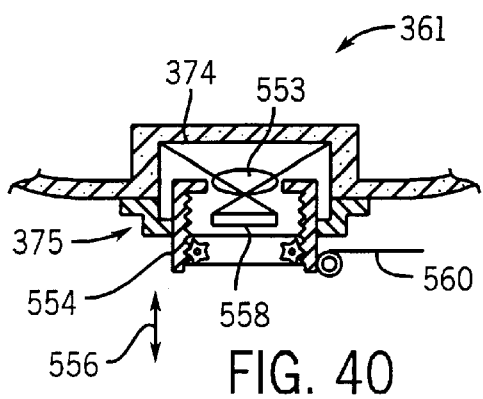
Figure 41:
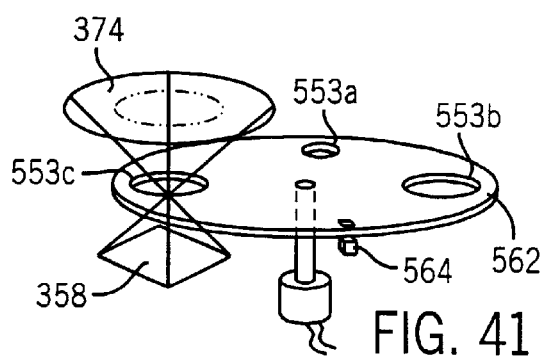
Figure 42:
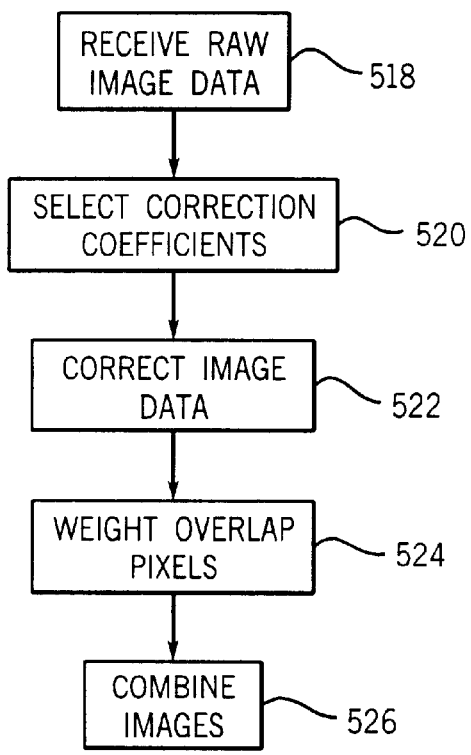
Figure 43:
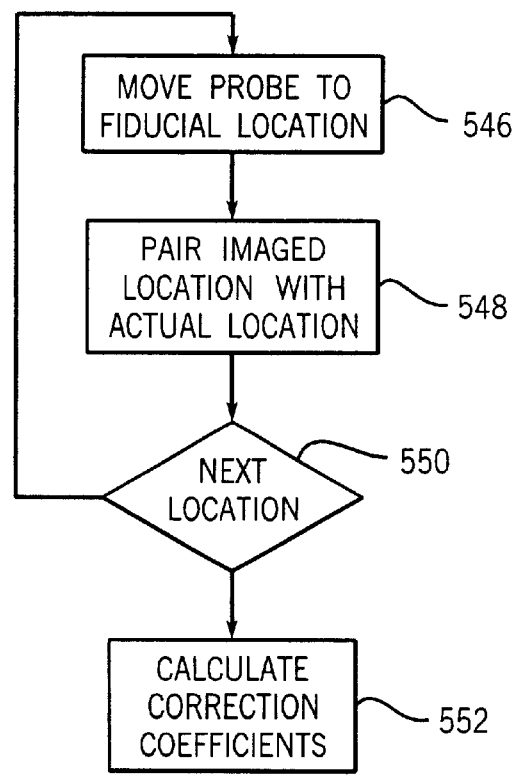

FIG. 27 is an enlarged, fragmentary view of FIG. 26 showing the alternative fitting of a forearm positioner or the foot positioner within a channel of the cradle along the path of x-rays between the x-ray source and x-ray detector;

FIG. 29 is a top plan view of the cradle of FIG. 25 but with the C-arm removed, showing the forearm positioner in use with a patient's arm;

FIG. 29 is a side elevational view of the cradle of FIG. 28;

FIG. 30 is a top plan view of the cradle of FIG. 28 but with the foot positioner in use with a patient's leg and showing the use of an auxiliary pancake image intensifier for use with fluoroscopy or other x-ray equipment not having suitable dual energy or digital imaging capabilities;

FIG. 31 is a cross sectional view of the pancake image intensifier of FIG. 30 with the protective shrouding removed and taken along a plane including the x-ray beam axis showing the compact, high distortion configuration and an attached processing computer;

FIG. 32 is a flow chart of software executed by a processing computer associated with the -x-ray detector for providing quantitative densiometric data;

FIG. 33 is a block diagram of the steps of scatter correction of the present invention;

FIG. 34 is a block diagram illustrating the removal of line correlated noise per the present invention;

FIG. 35 is a figure similar to that of FIG. 31 showing an alternative embodiment of an image intensifier using microchannel plates and a large area target screen;

FIG. 36 is a perspective view of two image intensifiers according to FIGS. 31 and 35 showing alternative cylindrical and rectangular designs;

FIG. 37 is a perspective view in partial phantom the a rectangular image intensifier design of FIGS. 35 and 36 employing multiple cameras to provide longer focal length lens systems, each camera producing a separate partial image of a square image;

FIG. 38 is a schematic plan view of two partial images per the cameras of the image intensifier of FIG. 37 showing slight barrel distortion in overlapping portions of the images;

FIG. 39 is a perspective view of an x-ray system employing a movable image intensifier such as may use different correction factors at different orientations and showing a computer controlled stereotactic device as may be used in conjunction with the image intensifier to measure the distortion of the image intensifier, FIG. 40 is a fragmentary cross-sectional view of the image intensifier as shown in FIG. 31 and the lens system contained therein for axial movement as part of a zoom lens system;

FIG. 41 is perspective view of an alternative lens positioner system allowing different magnifications of the optical image of the rear target to be obtained;

FIG. 42 is a flow chart of a program executed by the computer of FIG. 6 for selecting different correction factors dependent on different modes including those related to different lenses or orientations; and FIG. 43 is a flow chart of a program executed by the computer of FIG. 6 for calibrating the system shown in FIG. 39.

DETAILED DESCRIPTION OF THE INVENTION

C-arm Support Mechanism

Referring now to FIG. 1, an x-ray machine 10 per the present invention includes a generally box-shaped cart 12 having castors 14 extending downward from its four lower corners. The castors 14 have wheels rotating about a generally horizontal axis, and swiveling about a generally vertical axis passing along the edges of the cart 12. Castors 14, as are understood in the art, may be locked against swiveling and/or against rotation.

With one castor 14 locked and the others free to rotate and swivel, a pivot point 15 for the cart 12 is established with respect to the floor such as may be used as a first positioning axis 11 for the x-ray machine 10.

Positioned on the top of the cart 12 is a turntable 16 holding a video monitor 18 and attached keyboard 20 for swiveling about a vertical axis for convenience of the user. The video monitor 18 and the keyboard 20 may swivel separately so that one operator may view the video monitor 18 while a second operates the keyboard 20.

The video monitor 18 and the keyboard 20 allow for control of a computer 22 contained in a shelf on the cart 12 open from the front of the cart 12. The computer 22 may include a general microprocessor-type processor 23 and a specialized image processor 27 for particular functions as will be described. The computer 22 further includes a number of interface boards allowing it to provide control signals to various components of the x-ray machine 10 as will be described and to receive x-ray image data. In addition, the computer 22 receives signals from a foot switch 61 that is used to activate the x-ray system for a brief exposure. Control of the computer 22 may also be accomplished through a remote control wand 63 of a type known in the art.

Referring now also to FIG. 2, attached to the right side of the cart 12 is a horizontal slide 24 positioned to provide an attachment point 26 for an articulated arm 19 supporting a substantially circular C-arm 56, which in turn holds an x-ray tube 68 and an image intensifier 82 and camera 84, in opposition, and facing each other as will be described below. The function of the x-ray tube, the image intensifier and the camera are well known in the prior art in the use of mobile C-arm type x-ray devices used for image display and are described in U.S. Pat. No. 4,797,907 hereby incorporated by reference as part of the prior art. The C-arm may be mass balanced, that is to say its weight may be distributed to reduce its tendency to rotate through collar 54 so that minimal frictional pressure may be used to prevent it from moving.

The articulated arm 19 may be slid horizontally toward the front of the cart 12 to provide a second positioning axis 25 of the x-ray machine 10. A first pulley 28 is rotatively fixed in a vertical plane attached to the portion of the slide 24 that may move with respect to the cart 12, and is pivotally attached to a rigid arm 30 extending toward the front of the cart 12. The other end of the rigid arm 30 supporting a second pulley 32 is also mounted to swivel with respect to arm 30. A belt 34 wraps around a portion of the circumference of each of pulleys 28 and 32 and is affixed at one point along that circumference to each of the pulleys 28 and 32 so that pivoting motion of the arm 30 about the center point 26 of pulley 28 causes rotation of pulley 32 so that it maintains a fixed rotational orientation with respect to the cart 12 as pulley 32 and hence C-arm 56 is moved up and down along a third axis 37. The linkage, so created, is a variation of the "four bar linkage" well known in the art.

Helical tension springs (not shown for clarity) balance the pulley 32 in rotative equilibrium about point 26 against the weight of the articulated arm 19, C-arm 56, and other devices attached to the arm 19.

Attached to pulley 32 is a third pulley 36 extending in a generally horizontal plane perpendicular to the plane of pulley 32. The third pulley 32 is attached pivotally to a second rigid arm 40, which at its other end holds another pulley 38 positioned approximately at the midline 41 of the cart 12. The midline 41 symmetrically divides the left and right sides of the cart 12.

Portions of the circumference of pulleys 36 and 38 are also connected together by a belt 44 so as to form a second four bar linkage allowing pulley 38 to move toward and away from the cart 12, along a fourth positioning axis 45, with pulley 38 and C-arm 56 maintaining their rotational orientation with respect to cart 12.

Referring now to FIG. 4, pulley 38 includes a center shaft member 50 having a coaxial outer collar 52 to which belt 44 is attached. A stop 55 attached to the shaft 50 limits the motion of the collar 52 in rotation with respect to the shaft 50 to approximately 26 degrees. Frictional forces between shaft 50 and collar 52 cause shaft 50 to maintain its rotational orientation with respect to collar 52 and hence with respect to pulley 36 until sufficient force is exerted on shaft 50 to displace it with respect to collar 52. Thus pressure on the C-arm 56 can provide some pivoting motion of the C-arm about the axis of the pulley along a fifth positional axis.

Referring now to FIGS. 1, 3 and 4, attached to the shaft 50 is a C-arm collar 52 supporting the arcuate C-arm 56 curving through an approximately 180 degree arc in a vertical plane substantially aligned with the midline 41 of the cart 12 as has been mentioned. The shaft 50 may connect to collar 52 so that the latter may swivel in about a horizontal axis bisecting the circle of the C-arm 56. This axis may be aligned with the center of mass of the C-arm 56 so that there is not a self-righting tendency of the C-arm or the axis may be placed above the axis of the C-arm so as to provide for a beneficial self-righting action. This motion is orthogonal to that provided by motion of shaft 50 and may augment that provided by the castors 14. Techniques of balancing the C-arm in its various rotational modes, when this is desired, is taught by U.S. Pat. No. 5,038,371 to Janssen issued Aug. 6th, 1991 and hereby incorporated by reference as exemplifying the known prior art understood to all those of ordinary skill in the art.

As described above, motion of the collar 52 may be had in a vertical manner by means of the parallelogram linkage formed by pulleys 28 and 32 of the articulated arm 19 as shown in FIG. 2. Forward and backward motion away from and toward the cart 12 may be had by the second four bar linkage formed from pulleys 36 and 38. A slight pivoting of the C-arm 56 about a vertical axis slightly to the rear of the collar 52 and concentric with the axis of pulley 38 may be had by means of the rotation between collar 52 and 50 of FIG. 4. Greater rotation of the C-arm about the vertical axis passing through pivot point 15 may be had by rotation of the cart about one of its stationary castors 14. Thus, considerable flexibility in positioning the C-arm may be had.

Figure 5:
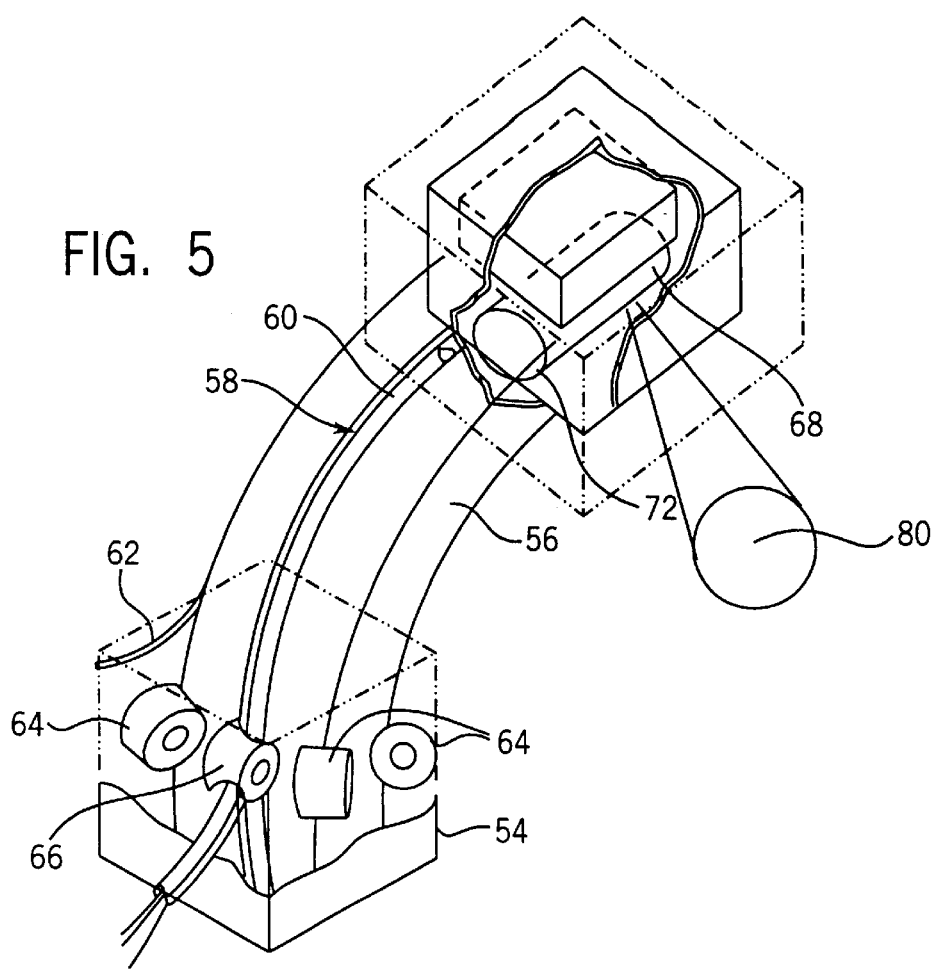
FIG. 5 is a detail view of the C-arm of FIG. 1 and the attached x-ray tube assembly showing the electrical cabling providing power to an x-ray tube power supply fitting into a groove in the C-arm and showing an abutment of the anode of the x-ray tube against the metal casting of the C-arm for heat sinking purposes.

Referring now to FIG. 5, the C-arm 56 is an aluminum casting having formed along its outer circumference a channel 58 into which a cable 60 may be run as will be described. C-arm 56 has a generally rectangular cross-section taken along a line of radius of the C-arm arc. Each corner of that rectangular cross-section holds a hardened steel wire 62 to provide a contact point for corner bearings 64 within the collar 52. The corner bearings 64 support the C-arm 56 but allow movement of the C-arm 56 along its arc through the collar 52.

A cable guide pulley 66 positioned over the channel 58 and having a concave circumference feeds the cable 60 into the channel 58 as the C-arm moves preventing tangling of the cable 60 or its exposure at the upper edge of the C-arm 56 when the C-arm 56 is rotated. The excess length of cable 60 loops out beneath the collar 52.

X-Ray Tube Cooling

Referring now to FIGS. 5 and 6, the C-arm supports at one end a generally cylindrical x-ray tube 68 having a cathode 70 emitting a stream of electrons against a fixed anode 72. The conversion efficiencies of x-ray tubes are such that the anode 72 can become quite hot and typically requires cooling. In the present invention, the anode 72 is positioned to be bolted against the aluminum casting of the C-arm 56 thereby dissipating its heat into a large conductive metal structure of the C-arm 56.

The x-ray tube 68 is connected to an x-ray tube power supply 74 which separately controls the current and voltage to the x-ray tube 68 based on signals received from the computer 22 as will be described. The control signals to the x-ray tube power supply 74 are encoded on a fiber optic within the cable 60 to be noise immune. Low voltage conductors are also contained within cable 60 to provide power to the x-ray tube power supply 74 from a low voltage power supply 76 positioned on the cart 12.

During operation, an x-ray beam 80 emitted from the x-ray tube 68 passes through a patient (not shown) and is received by an image intensifier 82 and recorded by a charge couple device ("CCD") camera 84 such as is well known in the art. The camera provides digital radiation values to the computer 22 inversely proportional to the x-ray absorption of the imaged object for processing as will be described below.. Each radiation value is dependent on the intensity of x-ray radiation received at a specific point on the imaging surface of the image intensifier 82.

Image Noise Reduction

Referring now to FIGS. 6 and 7, the data collected by the CCD camera 84 may be used to provide an image 86 displayed on video monitor 18. As will be described in more detail below, the CCD camera receiving a light image from the image intensifier 82 at a variety of points, provides data to the computer, which maps the data from the CCD camera 84 to a pixel 88 in the image 86. For convenience, the data from the CCD camera 84 will also be termed radiation data reflecting the fact that there is not necessarily a one-to-one correspondence between data detected by the CCD camera 84 and pixels 88 displayed on the video monitor 18.

The CCD camera 84 provides a complete set of radiation data for an entire image 86 (a frame) periodically once every "frame interval" so that real-time image of a patient placed within the x-ray beam 80 may be obtained. Typical frame rates are in the order of thirty frames per second or thirty complete readouts of the CCD detector area to the computer 22 each second.

Each frame of data is stored in the memory of the computer 22 and held until after complete storage of the next frame of data. The memory of the computer 22 also holds an average frame of data which represents an historical averaging of frames of data as will now be described and which is normally used to generate the image on the video monitor 18.

In a typical image 86, there will be some stationary object such as bone 90 and some moving object such as a surgical instrument 92 for example a catheter. In a second image 86' taken one frame after the image 86, the bone 90 remains in the same place relative to the edge of the image 86 and 86', however, the surgical instrument 92 has moved. Accordingly, some pixels 88' show no appreciable change between images 86 and 86', whereas some other pixels 88" show a significant change between images 86 and images 86'.

Figure 9:
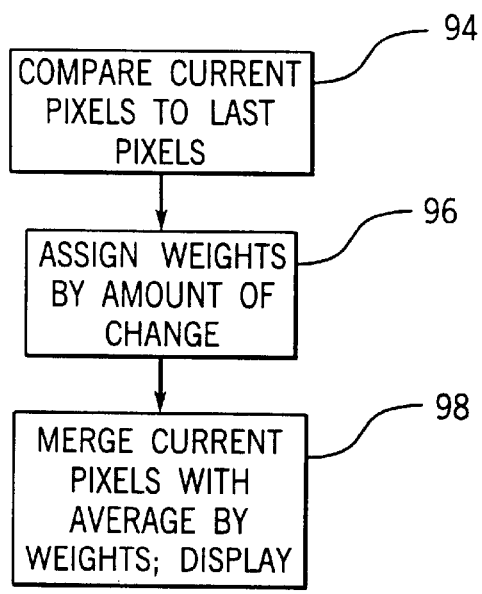
FIG. 9 is a flow chart of a method of the present invention providing differently weighted noise reduction to different areas of the image based on motion in the areas of the image.

Referring now to FIG. 9 as data arrives at the computer 22, the computer 22 executes a stored program to compare current pixels of the image 86' to the last pixels obtained from image 86 as indicated by process block 94. This comparison is on a pixel-by-pixel basis with only corresponding pixels in the images 86 and 86' compared. The difference between the values of the pixels 88, reflecting a difference in the amount of x-ray flux received at the CCD camera 84, is mapped to a weight between zero and one, with greater difference between pixels 88 in these two images corresponding to larger values of this weight w. This mapping to the weighting is shown at process block 96.

Thus pixels 88", whose value changes almost by the entire range of pixel values between images 86 and 86', receive a weighting of "one" whereas pixels 88' which have no change between images 86 and 86' receive a value of zero. The majority of pixels 88 being neither unchanged nor radically changed will receive a value somewhere between zero and one.

Generally, because the amount of x-ray fluence in the beam 80 is maintained at a low level to reduce the dose to the patient, the images 86 and 86' will have appreciable noise represented as a speckling in the images 86 and 86'. This noise, being of random character, may be reduced by averaging data for each pixel 88 over a number of frames of acquisition effectively increasing the amount of x-ray contributing to the image of that pixel.

Nevertheless, this averaging process tends to obscure motion such as exhibited by the surgical instrument 92. Accordingly, the present invention develops an average image combining the values of the pixels acquired in each frame 86, 86' in which those pixels in the current image 86' which exhibit very little change between images 86 and 86' contribute equally to the average image, but those pixels in the current image 86' that exhibit a great degree of change between images 86 and 86' are given a substantially greater weight in the average image. In this process, a compromise is reached between using historical data to reduce noise and using current data so that the image accurately reflects changes. Specifically, the value of each pixel displayed in the image is computed as follows.

$$P_i = (1-w)P_{i-1} + wP_{i,t} \quad (1)$$

where $P_{i-1}$ is a pixel in the previous average image, w is the weighting factor described above and $P_{i,t}$ is the current data obtained from the CCD camera 84. This effective merger of the new data and the old data keyed to the change in the data is shown at process block 98.

Image Intensifier Distortion

Figure 10:
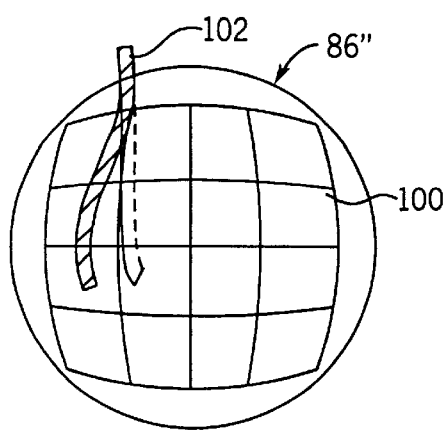
FIG. 10 is a figure similar to that of FIG. 7 showing an image of a rectilinear grid as affected by pincushion distortion in the image intensifier and video camera optics such as may provide a confusing image of a surgical tool being manipulated in real-time.

Referring now to FIG. 10, an image 86" of a rectilinear grid 100 positioned in the x-ray beam 80 will appear to have a barrel or pincushion shape caused by distortion of the image intensifier 82 and the optics of the CCD camera 84. During a real-time use of the image 86" by a physician, this distortion may cause confusion by the physician controlling a tool 102. For example, tool 102 may be a straight wire shown by the dotted line, but may display an image 86' as a curved wire whose curvature changes depending on the position of the tool 102 within the image 86. This distortion thus may provide an obstacle to a physician attempting to accurately place the tool 102 with respect to an object within the image 86'.

Figure 11:
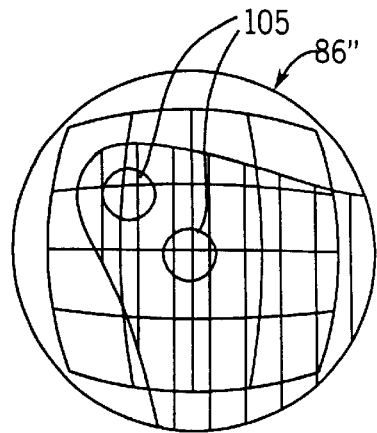
FIG. 11 is a figure similar to FIG. 10 showing equal areas of the image that encompass different areas of the imaged object, such variation as may affect quantitative bone density readings.

Referring now to FIG. 11, the distortion of image 86" also means that two equal area regions of interest 105 (equal in area with respect to the image) do not encompass equal areas of the x-ray beam 80 received by the image intensifier 82. Accordingly, if the data from the CCD camera 84 is used for quantitative purposes, for example to deduce bone density, this distortion will cause an erroneous variation in bone density unrelated to the object being measured.

Accordingly, the present inventors have adopted a real-time digital re-mapping of radiation data from the CCD camera 84 to the image 86 to correct for any pincushion-type distortion. This remapping requires the imaging of the rectilinear grid 100 and an interpolation of the position of the radiation data received from the CCD camera 84 to new locations on the image 86" according to that test image. By using digital processing techniques in a dedicated image processor 27, this remapping may be done on a real-time basis with good accuracy.

Referring to FIG. 19, there are two types of distortion, isotropic and anisotropic. Isotropic distortion is rotationally symmetric (e.g. like barrel and pin cushion distortion). Anisotropic distortion is not rotationally symmetric. Both types of distortion and rotation are so-called third order aberrations which can be written in the form:

$$Dx = r^2(Du - dv) \quad (2)$$

$$Dy = r^2(Dv + du) \quad (3)$$

where Dx and Dy are pixel shifts due to distortion; r is the distance from the correct position to the optical axis and D and d are distortion coefficients which are constant and u and v are correct pixel positions.

Referring also FIG. 2, received image 86 may exhibit pincushion distortion evident if an image 86 of the rectilinear grid 100 is made. The distortion is caused by the pixel shifts described above.

Equations 1 and 2 may be rewritten as third order two-dimensional polynomials, the case for equation (1) following:

$$x = (a_x + e_x v + i_x v^2 + m_x v^3) + (b_x + f_x v + j_x v^2 + n_x v^3)u + (c_x + g_x v + k_x v + o_x v^3)u^2 + (d_x + h_x v + l_x v + p_x v^3)u^3 \quad (4)$$

In these polynomials, $a_x$ and $a_y$ govern the x and y translation of the image, $e_x$ and $b_y$ take care of scaling the output image, while $e_y$ and $b_x$ enable the output image to rotate. The remaining higher order terms generate perspective, sheer and higher order distortion transformations as will be understood to those of ordinary skill in the art. Thirty-two parameters are required for the two, third order polynomials. These parameters may set manually or may be automatically extracted by a program executed by the computer in an off-line (non-imaging) mode after imaging the known grid 100 and comparing the distorted image of the grid 100 to the known grid 100 to deduce the degrees of distortion.

Referring now to FIG. 19 in a first step of the correction process, the grid 100 is imaged as indicated by process block 160 to determine the exact type of distortion present and to obtain values for the coefficients a through p of the above referenced polynomial equations.

At process block 166, these parameters may be input to the computer 22 and used at a transformation of received image 86 into image data 164 as indicated by process block 168. For rotation of the image 164, new parameters of the polynomials may be entered by means of hand-held remote control wand 63 shown in FIG. 1.

The transformation process generally requires a determination of the pixel shift for each radiation pixel 163 of the input image 86 which in turn requires an evaluation of the polynomials whose coefficients have been input. A number of techniques are known to evaluate such polynomials including a forward differencing technique or other techniques known in the art. These transformations provide values of u and v for an image pixel 170 corresponding to a particular radiation pixel 163.

After the transformation of process block 168, the u, v locations of the radiation pixels will not necessarily be centered at a pixel location defined by the hardware of the video monitor 18 which usually spaces pixels 170 at equal distances along a Cartesian axis. Accordingly, the transformed pixels must be interpolated to actual pixel locations as indicated by process block 172.

A number of interpolation techniques are well known including bilateral and closest neighbor interpolation, however in the preferred embodiment, a high-resolution cubic spline function is used. A given value of an interpolated pixel 170 ($P_{int}$) is deduced from a 4×4 block of transform pixels ($P_{i,j}$) in which it is centered as follows:

$$P_{int} = f(n-2)X_1 + f(n-1)X_2 + f(n)X_3 + f(n+1)X_4 \quad (5)$$

where:

$$X_i = f(m-2)P_{i,1} + f(m-1)P_{i,2} + f(m)P_{i,3} + f(m+1)P_{i,4} \quad (6)$$

where:

$$f(x) = (a+2)x^3 + -(a+3)x^2 + 1 \text{ for } x \in [0,1];$$

$$f(x)ax^3 + -5ax^2 + 8ax - 4a \text{ for } x \in [1,2]; \quad (7)$$

f(x) is symmetrical about zero. In the preferred embodiment a=−0.5 and where m and n are fractions indicating the displacement of the neighboring pixels $P_{i,j}$ with respect to $P_{int}$ in the x and y directions, respectively.

At process block 180, the transformed and interpolated image is displayed.

Noise Equalization

Figure 12:
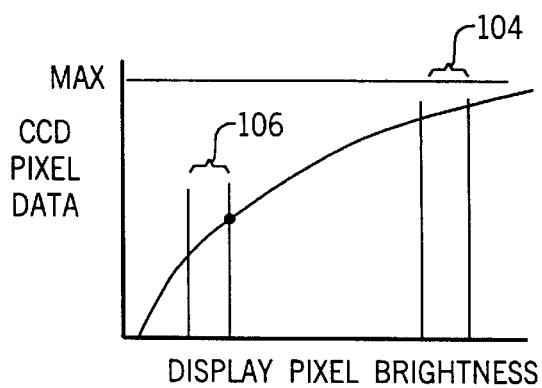
FIG. 12 is a plot of raw image data from the image intensifier/video camera as is translated into pixel brightness in the images of FIGS. 7, 8, 10, and 11 by the microprocessor of FIG. 6 according to a non-linear mapping process such as provides noise equilibrium in the images and maximum dynamic range for clinical data.

Referring now to FIG. 12, the radiation data from the CCD camera 84 are mapped to the brightness of the pixels of the image 86 according to a second transformation. In the preferred embodiment, this mapping between CCD radiation data and image pixel brightness follows a nonlinear curve 103 based on the hyperbolic tangent and being asymptotically increasing to the maximum CCD pixel value. This curve is selected from a number of possibilities so that equally wide bands of image pixel brightness 104 and 106 have equal amounts of image noise. The curve 103 is further positioned to provide the maximum contrast between clinically significant tissues in the image.

Exposure Control

The noise in the image 86 is further reduced by controlling the fluence of the x-ray beam 80 as a function of the density of tissue of the patient within the beam 80. This density is deduced from the image 86 itself produced by the CCD camera 84. In response to the image data, a control signal is sent via the fiber optic strand within the cable 60 to the x-ray tube power supply 74 positioned adjacent to the x-ray tube 68 (shown in FIG. 5). By positioning the x-ray tube power supply 74 near the x-ray tube 68, extremely rapid changes in the power supplied to the x-ray tube 68 may be obtained. Distributed capacitances along high tension cables connecting the x-ray tube 68 to a stationary x-ray tube power supply are thus avoided in favor of low voltage cable 60, and the shielding and inflexibility problems with such high tension cables are also avoided.

Automatic Technique Control

Figure 13:
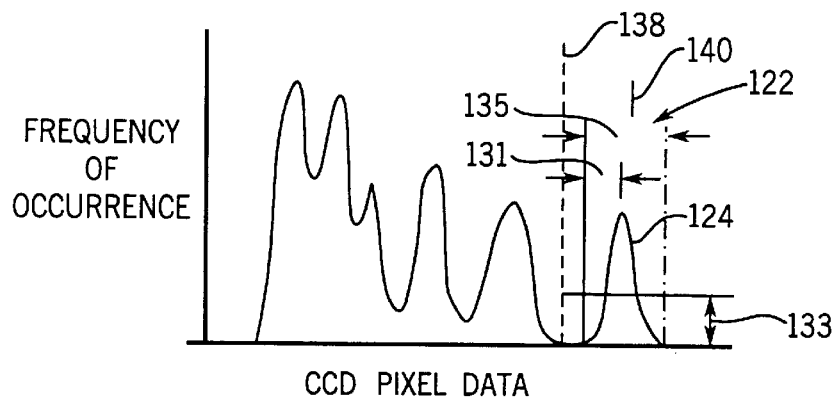
FIG. 13 is a histogram plotting values of data from the image intensifier/video camera versus the frequency of occurrence of data values showing an isolated Gaussian distribution at the right most side representing unattenuated x-ray values.
Figure 14:
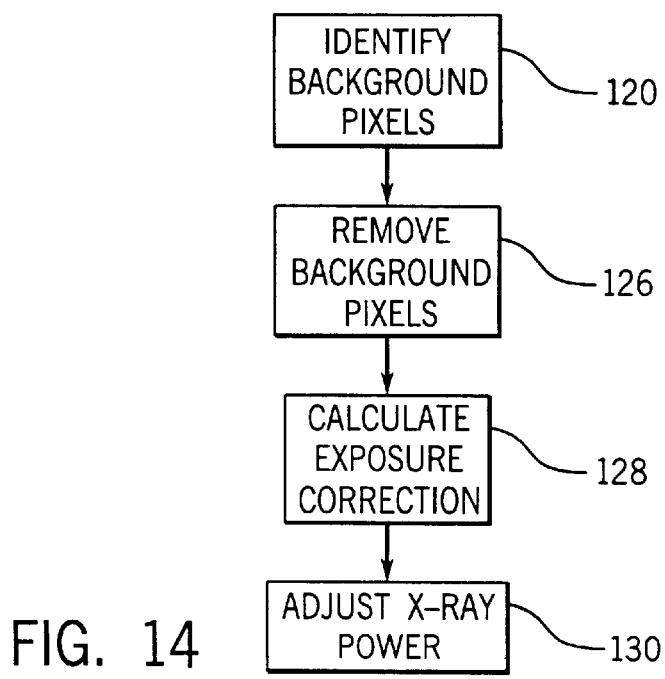
FIG. 14 is a flowchart describing the steps taken by the programmed microprocessor of FIG. 6 to identify background pixels and remove them from a calculation of exposure rate used for controlling the remote x-ray tube power supply of FIG. 6.
Figure 20:
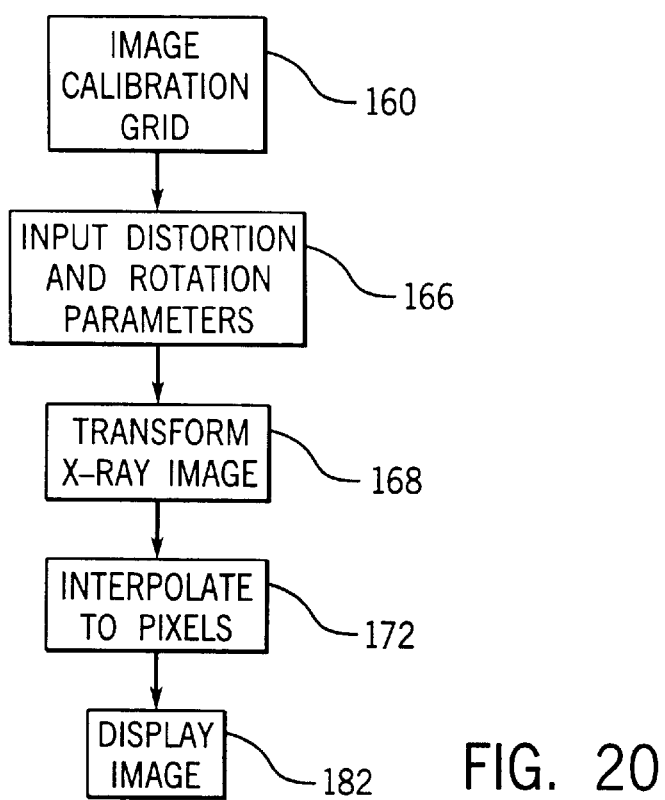
FIG. 20 is a flow chart of the steps performed by the computer in correcting and transforming the image of FIGS. 11 and 19.

Referring now to FIGS. 13 and 14, a determination of the proper control signal to send to the x-ray tube power supply 74 begins by analyzing the image data 86 as shown in process block 120. The goal is to provide for proper exposure of an arbitrary object placed within the x-ray beam 80 even if it does not fill the field of view of the CCD camera 84. For this reason, it is necessary to eliminate consideration of the data from the CCD camera 84 that form pixels in the image corresponding to x-rays that bypass the imaged object and are unattenuated ("background pixels"). These background pixels may be arbitrarily distributed in the image 86 and therefore, this identification process identifies these pixels based on their value. To do this, the computer 22 collects the values of the pixels from the CCD camera 84 in a histogram 122 where the pixels are binned according to their values to create a multiple peaked plot. The horizontal axis of the histogram 122 may, for example, be from 0 to 255 representing 8 bits of gray scale radiation data and the vertical axis may be a number of pixels having a particular value.

If there is a histogram value at horizontal value 255, and the maximum gray scale exposure recorded, the entire area of the histogram 122 is assumed to represent the imaged object only (no background pixels). Such a situation represents an image of raw radiation only or a high dose image of a thin object with possible clipping. In assuming that the whole histogram 122 may be used to calculate technique without removal of background pixels, a reduced exposure rate will result as will be understood from the following description and the peak classification process, to now be described, is skipped.

Otherwise, if there are no pixels with the maximum value of 225, the present invention identifies one peak 124 in the histogram 122 as background pixels indicated by process block 120 in FIG. 14. In identifying this peak 124, the computer 22 examines the histogram 122 from the brightest pixels (rightmost) to the darkest pixels (leftmost) assuming that the brightest pixels are more likely to be the unattenuated background pixels. The process block 120 uses several predetermined user settings as will be described below to correctly identify the peak 124.

Once the peak 124 has been identified, the pixels associated with that peak are removed per process block 126 by thresholding or subtraction. In the thresholding process, pixels above a threshold value 138 below the peak 124 are considered to be background pixels and are omitted from an exposure rate calculation. In the subtraction method, the peak 124 itself is used as a template to identify pixels which will be removed.

At process block 128, an exposure rate is calculated based on the values of the pixels in the remaining histogram data and at process block 130, an amperage and voltage value are transmitted via the cable 60 to the x-ray tube power supply and used to change the power to the x-ray tube. Generally, if the exposure rate is above a predetermined value, the amperage and voltage are adjusted to cut the x-ray emission from the x-ray tube, whereas if the exposure rate is below the predetermined value, the amperage and voltage are adjusted to boost the exposure rate to the predetermined value.

Figure 15:
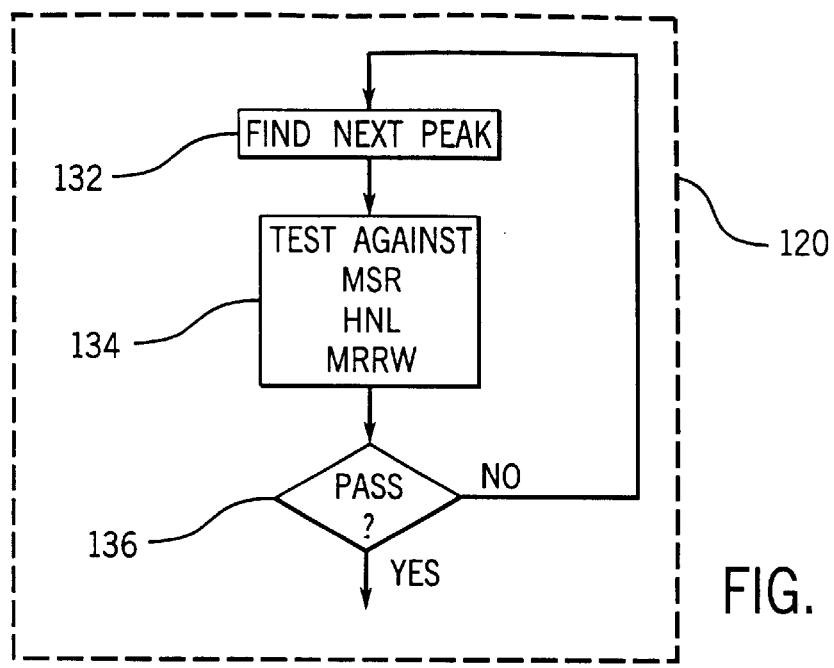
FIG. 15 is a detailed block diagram of the first block of the flow chart of FIG. 14.

Referring now to FIGS. 13, 14 and 15, the process of identifying background pixels will be explained in more detail. Process block 120 includes as a first step, an identification of a rightmost peak 124 in the histogram 122 (shown in FIG. 13) as indicated by subprocess block 132.

At succeeding subprocess block 134, this rightmost peak 124 is compared against three empirically derived parameters indicated in the following Table 1:

TABLE 1

| | |
|---|---|
| Minimum Slope Range (MSR) | Minimum necessary pixel range for which the slope of the peak must be monotonically increasing. |
| Histogram Noise Level (HNL) | Minimum height of the maximum value of the peak. |
| Maximum Raw Radiation Width (MRRW) | Maximum width of the detected peak with respect to the width of the entire histogram. |

Specifically at subprocess block 134, each identified peak 124 is tested against the three parameters indicated in Table 1. In the description in Table 1, "width" refers to the horizontal axis of the histogram 122 and hence a range of pixel values, whereas "height" refers to a frequency of occurrence for pixels within that range, i.e., the vertical axis of the histogram 122.

These first two tests, MSR and HNL, are intended to prevent noise peaks and peaks caused by bad imaging elements in the CCD camera 84 or quantization of the video signal in the A to D conversion from being interpreted as background pixels.

Peaks 124 with a suitable stretch of monotonically increasing slope 131 (shown in FIG. 13) according to the MSR value and that surpass the histogram noise level HNL 133 are evaluated against the MRRW parameter. This third evaluation compares the width 135 of the histogram 122 against the width of the entire histogram 122. The MRRW value is intended to detect situations where the imaged object completely fills the imaging field and hence there are no unattenuated x-ray beams or background pixels being detected. A valid peak 124 will normally have a width 135 more than 33% of the total width of the histogram 122.

At decision block 136 if the peak 124 passes the above tests, the program proceeds to process block 126 as indicated in FIG. 14. Otherwise, the program branches back to process block 132 and the next peak to the left is examined against the tests of process block 134 until a passing peak is found or no peak is found. If no peak is found, it is assumed that there are no background pixels and a raw exposure value is calculated from all pixels as described above.

Assuming that a peak 124 passes the tests of Table 1, then at process block 126 background pixels identified by the peak 124 selected at process block 120 are eliminated.

Figure 16:
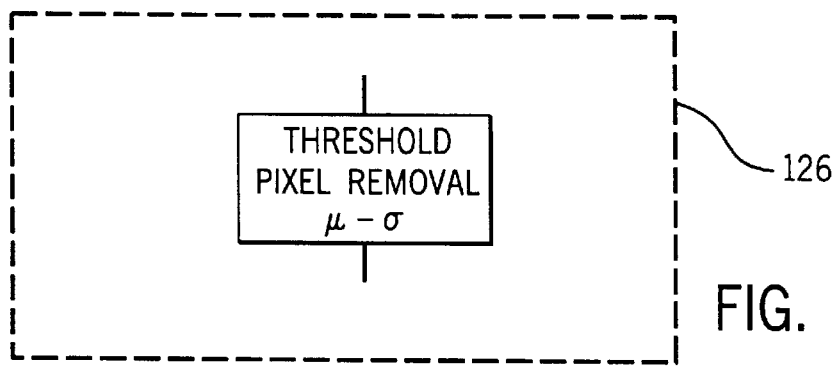
FIG. 16 is a first embodiment of the second block of the flow chart of FIG. 14.
Figure 17:
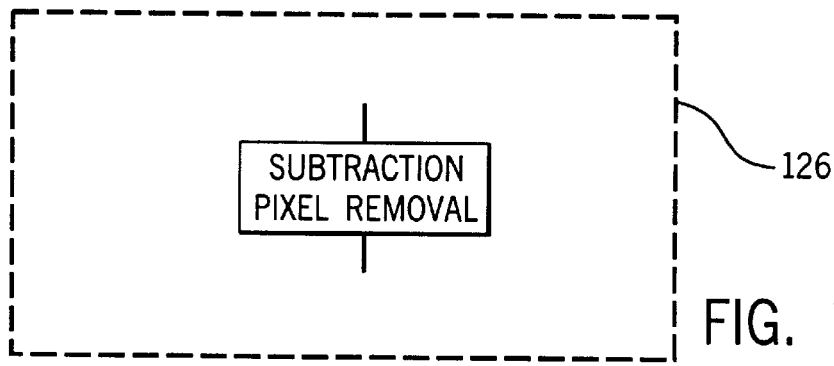
FIG. 17 is a second embodiment of the second block of the flow chart of FIG. 14.

In a first method of eliminating background pixels indicated at FIG. 16, a magnitude threshold 138 within the histogram 122 is identified. Pixels having values above this threshold will be ignored for the purpose of selecting an exposure technique. The threshold 138 is established by identifying the center 140 of the peak 124 (its maximum value) and subtracting from the value of the center, a value s being the distance between the start of the peak 124 as one moves leftward and the center 140. The area under the histogram 122 for values lower than the threshold 138 is computed to deduce a raw exposure value which will be used as described below.

In a second embodiment, the shape of the histogram peak 124 from the start of the peak as one moves leftward to its maximum 140 is reflected about a vertical line passing through the maximum 140 and subtracted from the histogram peak 124 to the left of the vertical line. This approach assumes that the peak 124 of the background pixels is symmetrical and thus this method better accommodates some overlap between the object pixels and the background pixels in the histogram 122. Again, the remaining pixels of the histogram 122 are summed (by integration of the area under the histogram 122 minus the area of the peak 124 as generated by the reflection) to provide a raw exposure value.

Figure 18:
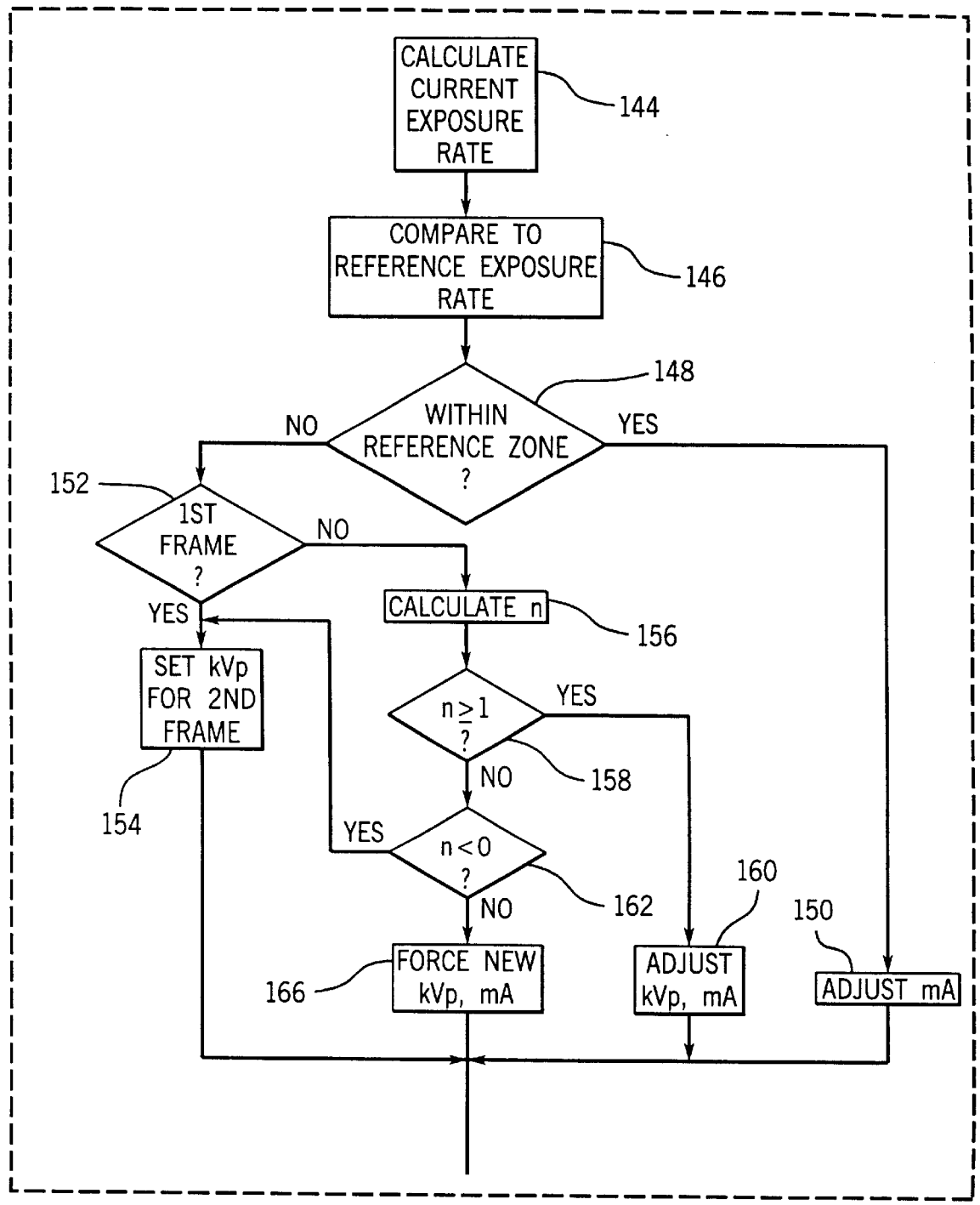
FIG. 18 is a detailed flow chart of the third block of the flow chart of FIG. 14.

Referring now to FIG. 18, the raw exposure value is transformed by the known transfer characteristics of the CCD camera (relating actual x-ray dose to pixel value) to produce a calculated current exposure rate as indicated at process block 144.

Referring to process block 146, the current exposure rate is next compared to a reference exposure rate, in the preferred embodiment being 1.0 mR per frame, however, this value may be refined after further clinical testing. If at process block 148, the current exposure rate is within a "half fine-tune range" of the reference exposure rate, then the program proceeds to process block 150, a fine tuning process block, and the amperage provided to the x-ray tube are adjusted in accordance to the disparity between the amperage and reference exposure rate. That is, if the current exposure is greater than the reference exposure rate, the amperage to the x-ray tube is reduced. The new value of amperage is compared against a predetermined range of amperage values (maximum beam current and minimum beam current values) so that the amperage value may never vary outside of this range.

If at decision block 148, the current exposure rate is outside of the half fine tune range established at decision block 148, a more substantial adjustment process is undertaken. Generally, the exposure provided by an x-ray system will follow the following equation:

$$X \approx s \cdot mA \cdot kVp^n. \qquad (8)$$

where:

s is seconds, mA is the amperage provided to the x-ray tube, kVp is the voltage provided to the x-ray tube, and n is a power factor dependent on the geometry of the machine and the particular kind of object being imaged.

Generally, the value of n will not be known in advance. Accordingly in the more substantial correction process, n is deduced by obtaining two different exposures for equal predetermined intervals with different kVp values so that the value of n may be deduced.

At decision block 152, it is determined whether a first or second reference exposure is to be obtained. If the first reference exposure was just obtained, the program proceeds to process block 154 and a new value of kVp is determined for a second exposure. In this case, the first exposure used will be that which was employed to produce the histogram 122 as previously described.

If the comparison of process block 148 indicated that the exposure rate was too high, a lower kVp value is selected; and conversely, if the exposure at process block 148 indicated the exposure was too low, an increased value of kVp is provided. The new kVp value for the second exposure must be within a predetermined range of kVp values established by the user. Mathematically, the kVp value selected may be described as:

$$kVp_2 = kVp_1 + a(dkVp) \qquad (9)$$

where a is a step factor and dkVp is a minimum practical change in tube voltage.

Two preferred means of selecting may be used: one providing linear and one providing logarithmic scaling. Such scaling techniques are well understood to those of ordinary skill in the art.

If at decision block 152, a second frame has already been taken with the new voltage value, then the program proceeds to process block 156 and the value of n in equation (9) is calculated. If the value of amperage is held constant between the first and second frame, the value of n may be determined according to the following equation:

$$n = \log X_2/X_1 / \log kVp_2/kVp_1 = kVp_1 \qquad (10)$$

where $X_1$ and $X_2$ are the measured exposure rates at the first and second frames, respectively, and $kVp_1$ and $kVp_2$ are the two x-ray tube voltages during the first and second frames.

At process block 158, this value of 'n' is checked against threshold values intended to detect whether an erroneous value of n has been produced as a result of 'clipping' in the radiation data used to calculate exposure. As is understood in the art, clipping occurs when an increased dose of an element of the CCD camera produces no increase in the camera's output.

At decision block 158, if the value of n calculated at process block 156 is greater than or equal to one, it is assumed to be valid and the program proceeds to process block 160 where kVp and mA are adjusted by setting mA equal to a maximum reference value and calculating kVp according to the following equation:

$$kVp_{new} = kV_{p2}(X_{ref} mA_2 / X_2 mA_{ref}) \qquad (11)$$

where $kVp_{new}$ and $mA_{new}$ are the settings for the next frame to be shot.

If the resulting kVp value conflicts with the minimum system, kVp, kVp is set to the minimum system value and mA is calculated according to the following equation using the mA and kVp value of the second frame.

$$mA_{new} = mA_2 X_{ref} / X_2 (kVp_2 / kVp_{min})^2 \qquad (12)$$

If the value of n in decision block 158 is less than one, then at process block 162, n is tested to see if it is less than zero. This value of n is realized when the exposure rate of the second frame changes in the opposite direction of the tube voltage. This suggests a clipped histogram and therefore the program branches back to process block 154 to obtain a new second frame. This condition may also arrive from object motion between the first and second frame.

On the other hand, if at decision block 162, n is not less than zero (e.g. n is between zero and 1), the program proceeds to process block 166. Here it is assumed that because the sensitivity of the exposure rate on change in kVp is low, there may be some partial clipping. New values of kVp and mA are then computed and used with the previous second frame values to calculate a new n as follows. Generally, if kVp and mA are high, they are both lowered and if kVp and mA are low, they are both raised.

Scatter Reduction

Referring now to FIG. 1, the image produced by the present invention may be used for quantitative analysis including, for example, that of making a bone density measurement. It is known to make bone density analyses from x-ray images through the use of dual energy techniques in which the voltage across the x-ray tube is changed or a filter is periodically placed within the x-ray beam to change the spectrum of the x-ray energy between two images. The two images may be mathematically processed to yield information about different basis materials within the image object (e.g. bone and soft tissue). For these quantitative measurements, it is desirable to eliminate the effect of scatter.

Figure 23:
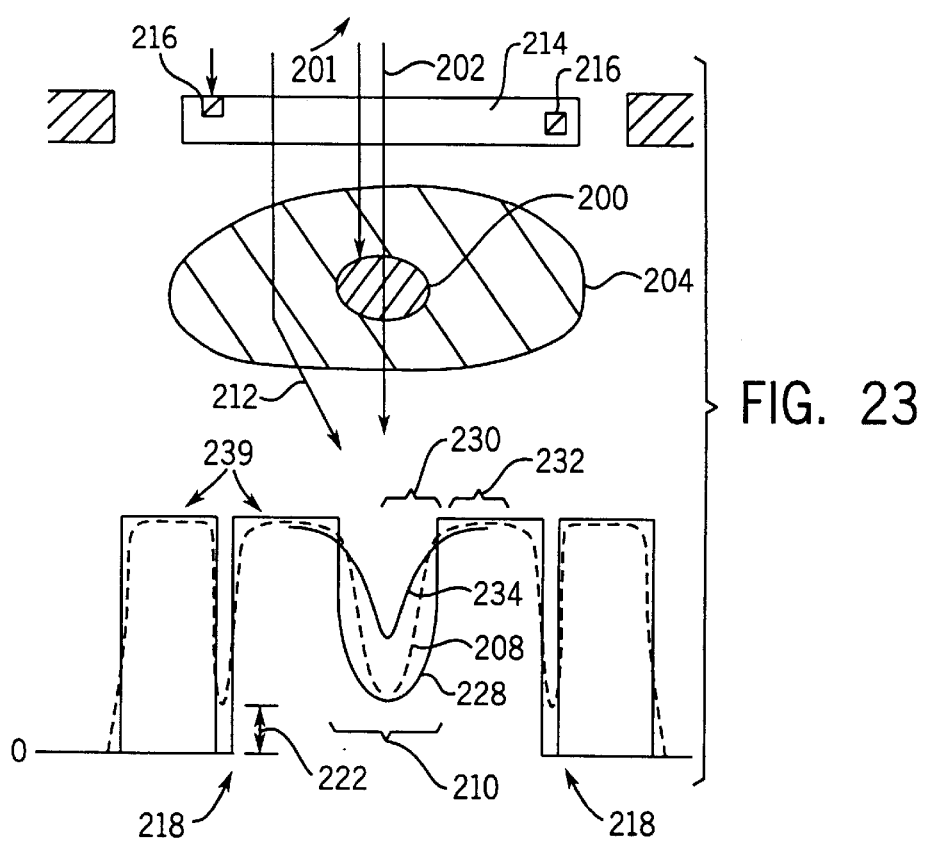
FIG. 23 is a cross-sectional view through the occluder of an imaged object of FIG. 21 along line 23—23, aligned with a graph depicting attenuation of x-rays as a function distance along the line of cross-section as well as theoretical attenuation without scatter and scatter components.

Referring now to FIG. 23 in imaging a patient's spine 200, for example, x-rays 202 are directed from an x-ray source 201 through the patient 199 to pass through soft tissue 204 surrounding a spine 200. Certain of the x-rays 202 are blocked by the spine 200 and others pass through the spine 200 to be recorded at the image intensifier 206. An attenuation image 208 measured by an image intensifier measures those x-rays passing through the patient 109.

A portion 210 of the attenuation image directly beneath the spine 200 records not only those x-rays 202 passing through the spine 200 and the soft tissue 204 above and below it, but also scattered x-rays 212 directed, for example, through soft tissue 204 to the side of the spine 200 but then scattered by the soft tissue to proceed at an angle to the portion 210 of the attenuation image 208 beneath the spine 200. Because the scattered x-rays 212 do not carry information about the attenuation of the spine 200, they are desirably removed from the image 208 prior to its use in quantitative measurement.

For this purpose, the present invention uses an occluder 214 being an x-ray transparent plate such as may be constructed of Plexiglas and incorporating into its body, a plurality of x-ray blocking lead pins 216. Preferably these pins are placed so as to project images 218 onto the image 208 received by the image intensifier 206 in positions outside an image 220 of the spine 200. Generally therefore, the pins 216 are placed at the periphery of the occluder 214. The pins 216 are sized so as to substantially block all direct x-rays from passing through them but so that their images 218 include a significant portion of scattered x-rays 212.

Figure 22:
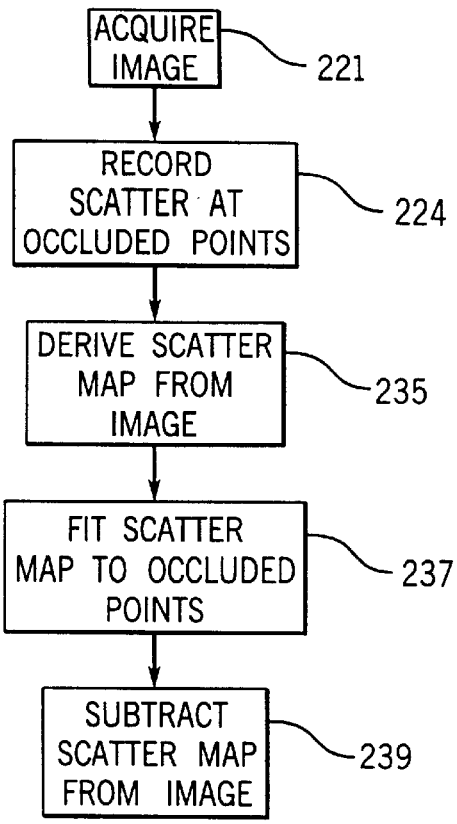
FIG. 22 is a flow chart of the steps of calculating and removing scatter using the occluder of FIG. 21.
Figure 21:
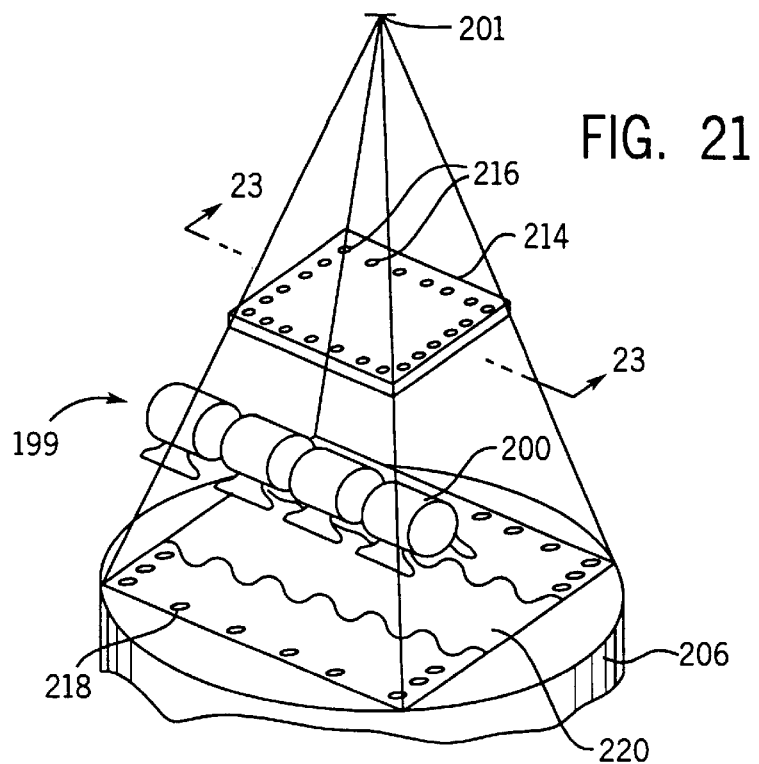
FIG. 21 is a perspective view of an occluder placed in an x-ray beam prior to an imaged object and used for calculating scatter.

Referring now to FIG. 22 at a first step of a scatter reduction operation with the occluder 214 of FIG. 21, an image is acquired of the imaged object, for example, the spine 200 and its surrounding soft tissue 204 (not shown in FIG. 21) including the images 218 of the pins 216. This acquisition is indicated by process block 221 of FIG. 22.

The pins 216 are held in predetermined locations with respect to the image 208 so that their images 218 may be readily and automatically identified. Preferably the pins 216 are placed at the interstices of a Cartesian grid, however, other regular patterns may be chosen. The image 208 may be corrected for pincushion-type distortion, as described above, so that the locations of the pins 216 may be readily located in the image based on their known positions in the occluder 214.

At each pin image 218, a value 222 indicating the magnitude of the received x-rays, shown in FIG. 23, may be ascertained. This value 222 measures the scatter received in the vicinity of image 218 caused generally by the effect of the soft tissue 204 and possible secondary scatter effects in the image intensifier 206. Values 222 are recorded, as indicated by process block 224, for each pin image 218. From these values, a set of normalizing points is established.

The image 208 is then used to derive a scatter map. Referring to FIG. 23, generally the amount of scatter at a given point will be a function of how many x-ray photons are received at points adjacent to the given point. For example, comparing the image 208 to a theoretical scatterless image 228 generally in an attenuated region 230 of the image 208 (e.g., under the spine 200), scatter will increase the apparent value in the image 208 as a result of radiation from nearby low attenuation regions scattering into the high attenuation region 230. Conversely the apparent value at a low attenuation region 232 will be decreased because of the scatter into the high attenuation region.

A map of the scattered radiation may thus be modeled by "blurring" the image 208. This blurring can be accomplished by a low pass filtering of the image 208, i.e., convolving the image 208 with a convolution kernel having rectangular dimensions corresponding to the desired low pass frequency cut off. The effect is an averaging of the image 208 producing scatter map 234.

The image used to produce the scatter map 234 is an attenuation image 208 obtained from the patient 199 without the occluder 214 in place, or may be an image 208 including the images 218 of the pins 216 but with the latter images 218 removed based on knowledge of their location. This removal of images 218 may substitute values of the image 208 at points 239 on either side of the images 218. The process of driving the scatter map from the image is indicated by process block 235 of FIG. 24.

Next as indicated by process block 237, the scatter map 234 is fit to the normalizing points 222 previously determined at process block 224.

Referring to FIG. 24, the scatter map 234 is thus normalized so that the portions 238 of the scatter map 236 located near the places where the images 218 would fall are given values 222 as determined at process block 224. This involves a simple shifting up or down of the scatter map 236 and may employ a "least square" fit to shift the scatter map 236 to multiple values 222 obtained from each pin 216. As adjusted, the scatter map 236 is then subtracted from the image 208 to eliminate or reduce the scatter in that image as indicated by process block 239.

The effect of subtracting a low pass filtered or blurred image properly normalized to actual scatter is to sharpen up the image 208 but also to preserve its quantitative accuracy. Thus the present invention differs from prior art scatter reduction techniques in that it both addresses the variation in scatter across the image caused by attenuation of x-rays by the imaged object but also incorporates accurate measurements of scatter in certain portions of the image.

DENSITOMETER ADAPTER

Referring now to FIG. 25, a mobile fluoroscopy machine 310 suitable for use with the present invention is similar to that which has been described above with respect to FIG. 1 with exceptions that will be apparent from context.

The mobile fluoroscopy machine 310 includes a mobile cart 312 supporting a computer 314 and monitor and keyboard 317 for receiving and processing digital x-ray image data The cart 312 supports on one side an articulating arm assembly 316 terminating in a rotatable C-arm 318. The C-arm supports, at the ends of the C, an image intensifier 320 and an x-ray source 322 opposed along an axis 324 so that the x-ray source 322 projects a cone-beam of x-ray radiation toward the image intensifier 320 along axis 324.

The articulating arm assembly 316 is connected to the C-arm 318 through one or more pivotal links 327 so that the axis 324 may be positioned to be horizontal approximately two feet above the floor to rest upon or be supported against the upper end of a supporting pedestal 326 or may be attached to the cart 312. Referring also to FIG. 26, the pedestal 326 includes a hemicylindrically concave cradle 328 at its upper surface to receive a lower portion of the cylindrical image intensifier 320 when the C-arm is so positioned to rest against the pedestal 326.

The pedestal 326 also provides on its upper surface a channel 330 extending across the axis 324 between the image intensifier 320 and the x-ray source 322 when the latter are positioned on the pedestal 326. The channel 330 may receive a limb positioner 332 such as may be adapted to support a patient's foot or arm across the axis 324 for densiometric measurement. The pedestal 326 may be weighted so as to provide a stable surface for support of the x-ray source 322 and image intensifier 320 and to provide adequate support for the patient's limb. The height of the pedestal 326 is selected to be suitable for either arm or foot imaging.

Referring now to FIGS. 27 and 30, the channel 330, extends substantially perpendicularly to axis 324 and has a horizontal bottom surface 333 pierced by two vertically extending guide holes 334 which may be used to receive and position corresponding pins 337 on one of two limb positioners 332. A foot positioner 336, as shown in FIG. 26, provides a padded calf support plate 338 fitting adjacent to the bottom surface 333 and an upwardly extending sole support 340 forming an obtuse angle with respect to the calf support plate 338. A cushion 342 on the calf support plate 338 may be adjusted so as to allow the patient's leg to extend at an angle from vertical for comfort. Gussets 344 span the angle between the sole plate 340 and calf support plate 338 to fix them in relative position but include apertures 346 to allow for the free passage of x-rays through a portion along axis 324 where the oscalcis of the heal will be located.

When positioned within the channel 330, the foot positioner 336 is also supported by upwardly extending channel sidewalls 348 which serve further to provide an alignment surface for the imaging face of the image intensifier 320 or other detector array and on the other side, an alignment surface for an emitting face of the x-ray source 322. Channel sidewalls 348 are generally radio translucent so as to permit the passage of x-rays therethrough, but may include: calibration materials such as are well known in the art for calibrating dual energy devices, antiscatter grids also well known in the art, or occluders for evaluating scatter as have been described above or in the parent applications hereby incorporated by reference.

Referring to FIGS. 27 and 28 for forearm imaging, the foot positioner 336 is removed and a palm support 352 is inserted by means of pin 337 in one of the holes 334 so as to locate a user's arm resting against the bottom surface 333 with the user's palm against the palm support 352 such that the bones of the forearm are placed along the axis 324 for imaging.

Referring to FIGS. 28 and 29, the hemispherical support cradle 328 may include three radially inwardly extending ribs 354 attached by means of screws or the like to be replaceable. Two of the ribs 354 are positioned in a horizontal plane to substantially bisect the image intensifier 320 when it is placed within the cradle 328. The third rib 354 is positioned at the bottom of the cradle 328 and is opposed by a rotating locking collar 358 which may be used to further secure the image intensifier 320 within the cradle 328. The front edge of the image intensifier is abutted against the upright face of the dividing barrier so as to precisely locate it along axis 324. The inner edges of these ribs 354 define an inner radius 356 of lesser diameter than the cradle 328 that by proper design of the ribs 354 may be adjusted to conform to the outer surface of a particular image intensifier 320.

Referring now again to FIG. 30, some fluoroscopy equipment will not permit digital imaging or the necessary dual energy control needed for densitometry. Accordingly, an independent detector array 360 may be placed within the cradle 328 in lieu of the image intensifier 320. This detector array 360 may be a pair of stimulable phosphor plates as are understood in the art with intermediate filtering so as to provide dual energy readings with a polychromatic x-ray source. In this way a switching of voltage on the x-ray source 322, as described above, can be avoided. Alternatively, the detector array 360 may be a large area solid state detector or scanning detector assembly such as are understood in the art including those constructed of amorphous silicon and thin film transistor technology or those employing active pixel technology in which CMOS integrated circuit fabrication techniques are employed. These detectors may be used with a switched x-ray source 322 to provide dual energy imaging or may be used in a stacked configuration with intermediate filtering so as to provide separate energy measurements, or may be used in a side-by-side configuration with interleaved detector elements filtered so as to be selectively sensitive to different energies.

In the preferred embodiment, and as shown in FIG. 31, the independent detector array 360 is a "pancake" image intensifier 361, suitably small so as to fit within the space between a conventional image intensifier 320 and the x-ray source 322. Referring to both FIGS. 30 and 31, the pancake image intensifier 361 includes a vacuum bowl 362 having a planar front surface 364 for receiving x-rays 366 (normally through the channel sidewalls 348 of the stand 326).

According to conventional design, the x-rays 366 pass through the front surface 364 of the vacuum bowl 362 to strike a target material 368 to eject electrons 370 into the volume of the bowl 362. Focusing electrodes 372 direct the electrons to a target phosphor 374 where an image is formed to be received by imaging array 375 such as a CCD array, video tube, active pixel array or other similar image recording material. The image area of the target phosphor 374 is much smaller than the front surface 364 so as to reduce the image size to one compatible with the camera. In the present invention the distance B between the target material 368 and the imaging array 375 (including any optical path through one or more focusing lenses) is less than or equal to the radial dimension A of the front surface 364, giving the pancake image intensifier 361 an extremely short-form factor suitable for practice with the present invention.

Hitherto, such form factors were avoided because they are known to result in severe distortion of the image formed on the target phosphor 374. This distortion is accommodated in the present invention by means of digital image processing in computer 314 which receives digitized pixel data from scanning electronics 378 connected to the imaging array 375 and corrects it according to the correction process described above with respect to the pincushion correction. Accordingly, the addition of digital signal processing allows for production of pancake image intensifier 361 in which the separation of the imaging optics from the front of the image intensifier is much reduced.

The above adapter may be modified to use in femur imaging. In this case the pedestal 326 may be eliminated in favor of a positioner (not shown) attached to the image intensifier 320 or x-ray source 322 directly. In the former case, the positioner may provide for a fixed air gap between the patient and the image intensifier 320 to reduce received scatter. So as to allow free manipulation of the C-arm 318, the positioner may be a lightweight plastic radiolucent material and may optionally include a calibration system such as a; flip in phantom for calibration of the dual energy readings and occluders for scatter correction as has been described above. Collimation and/or a separate solid state dual energy image detectors may also be held by the positioner whose outer surface may guide the positioning of the C-arm 318 to the necessary orientation which need not be horizontal but may be vertical for forearm measurements or the like. For femur measurements, the patient may stand and the C-arm 318 manipulated appropriately as guided by the positioner.

Referring now to FIGS. 31 and 32, computer 314 includes a processor 380 and memory 382, the latter of which receives raw image data in the form of pixels having spatial locations and brightness values forming images 384. Memory 382 also includes a processing program 386 providing a general interface and control of the operation of the fluoroscopy machine 310 and a processing of images 384 so as to provide a quantitative measure of bone isolated from soft tissue.

The processing program 386 can be simply loaded into the computer 314 for the fluoroscopy machine 310 when the pedestal 326 is to be employed with a fluoroscopy machine 310 providing digital imaging and x-ray voltage control. If an independent detector array 360 is required, the program 386 may be executed on a computer 314 associated with that independent detector array 360.

At a first step in the program 386 indicated by process block 388, the operator of the fluoroscopy machine 310, having indicated a desire to perform densitometry and having positioned the C-arm in the pedestal 326, enters patient data that will be used to identify the image 384 to be collected.

At succeeding process block 390, data is collected for three distinct images 384 with: 1) no x-ray exposure, 2) high energy x-ray exposure, and 3) low energy x-ray exposure. Each of the exposures is preserved as a separate image file in the memory of the computer 314. The first exposure is used for correction routines to be described; the latter two exposures are used to deduce bone density according to methods well known in the art in which variations in high energy and low energy absorption are used to deduce the Compton scattering and atomic number of the material lying between the x-ray source 322 and the image intensifier 320. As is understood in the art, these two measurements allow the amount of bone as opposed to soft tissue located in that image region to be accurately measured. The data is acquired directly from the independent detector array 360 or in the event that stimulable plates are used, a reader may be attached to the computer 314 so as to acquire the necessary pixel data of an image 384. In the same way a conventional photographic film/filter plate arrangement may be used.

At next process block 393, each of these images is corrected for non-linearity of the detector such as may be determined empirically at an earlier time by testing the detector according to methods well known in the art, and which is a function of the detector and the technology used by the detector. Generally the testing exposes the detector to different fluences of x-rays and measures the output of the detector and the correction is intended to ensure that, for example, a doubling of fluence results in a doubling of detector output after correction. The correction is generally simply a scaling of each of the images by a factor that is a function of the pixel value for each pixel and possibly the location of the pixel.

At process block 395, noise related to the particular line of the detector is removed. Referring to FIG. 34, the imaging array 375 provides a matrix of detector elements 392 arranged in rows and columns. Normally, either rows or columns are ganged together to be read out by dedicated read out electronics 391 spanning a particular row or column. The read out electronics introduces noise which is imposed upon each detector element 392 of that row and which is thus line correlated, that is, more highly correlated with other detector elements 392 of the line than detector elements 392 of different lines. To eliminate line correlated noise, one detector element 392 in each line is blocked by a lead mask 394 so as to be shielded from x-rays. A pixel value 396 from this blocked detector element 392 will provide a value that varies according to the line noise. Thus a line correlated noise value 398 may be deduced and subtracted from the pixel values 400 of the other detector elements 392 in the line.

Referring again to FIG. 32 at a succeeding process block 402, veiling glare is removed and the field is flattened. This former correction attempts to eliminate blurring of the image such as may be caused by scatter or similar effects within the imaging array 375. Glare refers generally to a reading that would be obtained under detector elements 392 that were wholly shadowed by an occluding absorber on the surface of the imaging array 375. The glare is a function of the detector technology and is reduced by a deconvolution process based on an empirically derived deconvolution kernel according to a number of techniques well known in the art.

Also at process block 402 the field is flattened which is to say the gain variation of the detector elements 392 are normalized according to an empirically derived normalization map determined at the factory by exposing the detector to a uniform x-ray elimination and noting variation and intensities reported in the pixel values 400. At this time, dark currents from the detector elements 392 may also be eliminated as determined from the no-exposure x-ray image taken at process block 390.

Referring now to process block 404, a dynamic scatter correction may be employed as has been previously described with respect to FIGS. 21–23. Alternatively referring also to FIG. 33, a dynamic scatter correction may be employed in which the data of the image 384 is analyzed so as to create a histogram 406 of pixel values 400 for the entire image. The histogram may be divided into regions 408 (five equal regions in the preferred embodiment) corresponding roughly x-ray paths through: 1) air-only, 2) thin tissue, 3) thick tissue only, 4) thin bone and, and 5) thick-bone. Each of these materials will exhibit a different scattering and hence a different empirically derived scatter kernel 410 may be assigned to each region 408 with generally the lower density regions having narrower kernels commensurate with less scatter.

The selected scatter kernel 410 may be scaled by the pixel value of the image 384 on a pixel-by-pixel basis and that kernel, so scaled, applied to a deconvolver 412 used to deconvolve the image 384 to produce a deconvolved image 414. A number of techniques of deconvolution are well known in the art using a fixed scatter kernel and these same techniques may be used with the variable scatter kernel 410 described here. During deconvolution the kernel 410 will be sequentially applied to a set of adjacent pixel values determined by the width of the kernel. The center pixel value at any step of the deconvolution will be used to scale the kernel and to identify the region of the histogram for the purpose of selecting the kernel 410. In an alternative embodiment, the kernel may be fixed and simply scaled by the value of the centermost pixel during de-convolution.

Referring again to FIG. 32 at process block 416, the images 384 are log corrected reflecting the fact that attenuation is exponentially related to thickness. The images are now related to thickness, a dimension which will be important in the ultimate bone density determination.

At following process block 418, speckle may be identified for certain x-ray detectors 360 that are subject to extremely high readout values caused by noise which is possibly related to direct x-ray irradiation of the detector element. Speckle is identified by a simple thresholding process.

At next process block 420, path length correction may be performed based on the geometry of the particular C-arm such as may vary path length and magnification across the image as is well understood in the art.

Similarly at succeeding process block 422, beam hardening, the well known effect of a spectral shift in a polyenergetic x-ray beam as it passes through different thicknesses of material, and a Heel effect correction may be made, the Heel effect correction referring to a variation in the spectrum of an x-ray beam as a function of its angle in the cone of x-ray beams. Both of the corrections are known in the art, but must be employed in the present invention in order to provide suitable quantitative accuracy for densitometry.

At process block 424, the identified speckle of process block 418 is corrected by eliminating these identified pixels from subsequent calculation or by replacing them with a local average value.

The entire image may then be averaged or low-passed filtered at process block 426 so as to further reduce noise and to eliminate unneeded resolution.

The images are then processed according to well-understood techniques to produce a bone mineral density value at process block 428. This bone mineral density value indicates the amount of bone material at each pixel of the image largely independent of surrounding soft tissue. The pixel image may be analyzed in a number of methods but most simply, as indicated by process block 430, by defining either automatically or manually a desired region of interest within the image and making a measurement of total bone density within that region. Automated techniques may look for a local maximum or minimum of bone density or may use image recognition type techniques to locate reproducibly a particular region of the forearm or os calcis. Morphometric analysis may be applied to the image to detect bone fracture and other techniques such as texture analysis may be performed according to methods well known in the art. The results of the analyses and images so processed may be displayed by the computer 314.

Referring now to FIG. 35, in an alternative design for an image intensifier 361, the target material 368 receiving x-rays abuts an image intensifier employing one or more microchannel plates 500 which collect ejected electrons from the target material 368 to amplify and direct them against a target phosphor 374. The target material 368 includes, as is well known in the art, a phosphor layer and a photo cathode layer.

The target phosphor 374 is substantially the same size as the target material 368, so the image formed on the target phosphor 374 must be reduced to be captured by a CCD imaging array 375 of substantially smaller area. For this purpose, a lens system 502 (represented as a single lens but which may in fact be multiple lenses) projects an image from phosphor 374 on the imaging array 375.

As described above with respect to FIG. 31, the imaging array 375 may be at a focal plane a distance B behind the target material 368. The target material 368, in turn, may have a width A that is greater than or equal to depth B. Thus an image intensifier with a short form factor may be produced without the need for the focusing electrodes 372 described with respect to FIG. 31.

Although this design reduces the distortion caused by focusing of the electrons, a distortion may be introduced by the imaging of lens system 502 as is well known to those of ordinary skill in the art optics and resulting from a relatively short focal length. Accordingly, the same correction techniques described above to correct distortion introduced by the focusing electrodes may be applied to the digital signals received from the imaging array 375 of FIG. 35 to correct for the distortions introduced by the optical path between target phosphor 374 and imaging array 375.

Referring to FIG. 36, the invention does not require that a particular shape of target material 368 be used and both conventional circular areas of target material 368 and rectangular or square areas of target material 368 may be used. In the former case, the dimension A will be a diameter and in the latter case the dimension A may be a diagonal.

Referring to FIGS. 37 and 36, a rectangular target and in particular a square target provides additional challenges for either focusing of electrons per the mode of FIG. 31 or with optical focusing per the design of FIG. 35. Traditionally, optical imaging of square formats uses so-called cylindrical optical elements that are appropriately masked for a square field of view. The present invention allows more efficient use of optical elements and the use of longer focal length optical elements (with lower distortion) by providing multiple cameras 504 that may image different quadrants 506 of the target phosphor 374. While the present invention corrects for distortion, excess distortion may result in a loss of image resolution in the corrected image and thus is best minimized. This is particularly important with a reduced dimension B as constrains the focal length of the lenses 508 of the cameras 504. Breaking of the image of target phosphor 374 into quadrants 506 allows a longer focal length and thus lower distortion.

The multiple cameras 504 are positioned beneath a microchannel plate 500 under a rectangular target material 368. The optical axis of each camera 504 is centered on its respective quadrant 506. In the illustrated embodiment, the quadrants are positioned to divide the generally square target phosphor 374 and its optical image into four equal squares.

Referring now to FIG. 38, it will be understood that each of the four cameras 504 produces a separate image. For purposes of explanation, two of these images 510 and 510' will now be described.

Each of these images 510 and 510' will be square commensurate with the underlying detector array of the camera 504 used. Nevertheless, there will be some degree of distortion in the images 510 and 510' which will prevent a straightforward assembly of the images 510 and 510' together. This distortion may cause the images 510 and 510' to map to non-rectilinear boundaries 513 of the image on the target phosphor 374. Accordingly, the images 510 and 510' may be corrected for distortion before they are combined. This correction simplifies the combination process, however, it will be understood the combination process may alternatively precede the correction process.

After correction, images 512 and 512' will generally overlap both because of the correction and for reasons of mechanical and optical tolerances. An area of overlap 514 may thus be defined between any two images 510 and 510' which must be accounted for when the images are combined. Generally the combining will map each pixel or picture element of the images 510 and 510' into a corresponding pixel of a much larger image subtending all four quadrants 506. In the region of overlap 514, the pixels must be de-weighted and combined so as not to have undue influence in the ultimate contiguous image.

These processes may be completed by the computer 23 according to the steps shown in FIG. 42 to which reference is now made. At process block 518, raw image data is acquired by each of the cameras 504 at a focal plane as has been described before. The data will be digitized according to conventional methods either by circuitry associated with the camera 504 or by a separate analog to digital converter associated with the computer 23.

At a succeeding process block 520, a correction coefficient is selected for each of the raw images received. Thus it is not assumed that the cameras 504 produce the same degree of distortion of the image and a separate correction may be applied to each image 510 and 510'. As described before, such corrections remove pin cushion or barrel distortion providing that boundaries of the quadrants 512 lie in perpendicular directions along straight lines within the images 510 and 510' (even though the boundaries of the corrected images may no longer be rectilinear) with fidelity to the actual image on the surface of phosphor 374. As shown in FIG. 42, this correction process is process block 522.

At process block 524, pixels in the region of overlap 514 are de-weighted for example by 50% where only two images 510 and 510' overlap. However, it will be understood that more complex weighting systems providing, for example, greater weighting toward pixels closer to the center of a given image may be used.

The weights may be applied to the pixels in the region of overlap 514 according to the known geometry of the cameras 504 or overlapping or corresponding pixels may be determined by a correlation process in which the electronic images 510 and 510' (after correction) are slid with respect to each other until the highest degree of correlation is obtained.

At process block 526, the corrected and weighted images are then combined to form a single continuous image such as may be displayed on display 18 or printed on film or the like.

Referring now to FIG. 39, extremely low distortion image intensifiers 361 may be desirable for use in stereotactic procedures using a probe 528 and is manipulable by a three-dimensional motorized carriage 530 of a type well known in the art. Such a device may be used, for example, in maneuvering a biopsy needle to the site of a tumor as imaged by the image intensifier 361. In this case, the computer 22 may receive image data from the image intensifier 361 at an imaging module 532 implemented in one embodiment in software in the computer 22 and may provide control signals to the carriage 530 via a controller 534 also implemented in software.

In order to detect distortion in the image produced by the image intensifier 361, the tip of the probe 528 may be positioned along the axis between the x-ray source 68 and the front surface of the image intensifier 361 and may be stepped in a raster pattern 536. The x-ray source may be activated to provide an image of the tip of the probe 528 at the image intensifier 361.

The measured location of the tip of the probe 528 in the image produced by the image intensifier 361, as read by the imaging module 532, may be compared to its probe's exact physical location as determined by the controller 534 to deduce a set of correction coefficients 538. These correction coefficients 538 may be entered into a correction table 540 held in the computer 22 and used to correct images formed by the image intensifier 361. Thus automatic calibration of the correction factor is needed for the coefficients described above for image correction may be produced.

This system may also provide an indication of the corresponding pixels in the region of overlap 514 shown in FIG. 38 such as may be more difficult to obtain with a conventional grid calibration system as described above. Ideally the probe 528 for this purpose is radiolucent except at a tip so as to produce a single point-like image at the image intensifier 361.

The table 540 may be divided into records, each of which hold different coefficients for different modes of operation. The table 540 may contain records holding coefficients associated with different cameras 504 as described above with respect to FIG. 37.

Alternatively, the different records may be associated with possibly different image distortions caused, for example, by a local magnetic field that may result in different locations and orientations 542a and 542b of the image intensifier 361 producing different distortions. The particular orientations 542a and 542b may be determined by a position sensor 544 of a type well known in the art.

Referring now to FIG. 43, the calibration system may be performed by the imaging module 532 in computer 22 operating according to a stored program beginning at a process block 546 where the probe is moved to a particular fiducial point. At process block 548, the measured point in the image produced by the image intensifier 361 is compared to the actual physical location provided by controller 534 and an error determined. At process block 550, these process blocks 546 and 548 are repeated until a number of measurements have been made over the surface of image intensifier 361. After those measurements are complete at process block 552, the errors are used to deduce the coefficients as described above.

Referring now to FIG. 40, a lens 553 focuses the image on the imaging array 375 of the image intensifier 361 of FIG. 31. That lens 553 may be held by a lens support mechanism 554 providing for an axial motion of the lens as indicated by arrows 556 such as changes the magnification of a projected image upon a CCD 558 from the target phosphor 374. A simplified system is shown for clarity. As will be understood in the art, an actual system will require compensatory movement of the array 375 or additional lens elements.

This change in magnification may allow a zooming feature useful for providing higher resolution and greater magnification images produced by the image intensifier without movement of the image intensifier. The zooming may also introduce additional optical distortions and thus the actuator may provide or respond to a mode signal 560 which is also provided to the computer shown in FIG. 39 to select the appropriate coefficients from table 540 according to position of the lens 553 by the lens support mechanism 554.

Referring now to FIG. 41 in an alternative embodiment, multiple lenses 553a through 553c are held in a rotatable carriage 562 the latter which may rotate the lenses 553a through 553c into position between the target phosphor 374 and the imaging array 358. Lenses 553a through 553c may be combinations of lens elements and/or may combine with other stationary lens elements (not shown) to form the image. A rotation sensor 564 provides a mode signal to the computer 22 to indicate the correction factors 538 in table 540 for the appropriate lens 553a through 553c.

The short form factor detector of the present invention can be applied in a wide variety of applications where conventional image intensifier systems are used and is particularly useful in applications where maneuverability or reduced size is important. The low distortion possible with this system makes it particularly suited for procedures where the location of instruments within the body must be accurately determined including stereotactic procedures, guided needle biopsies, catheterizations, and the like. The present invention may also be used in recent procedures in which a needle must be guided into a vertebra for injection of stabilizing compounds into the osteoporotically weakened vertebral cavity. The present invention may also be used in industrial applications where low distortion, and/or compact size is desired.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claim.

We claim:
1. An imaging x-ray detector comprising:
   (a) an image intensifier having:
      (i) a front target receiving x-rays to eject electrons into an internal volume of the image intensifier;
      (ii) an electron amplifier receiving the ejected electrons to amplify the same;
      (iii) a rear target receiving the amplified electrons to produce an optical image;
   (b) at least two digital cameras directed toward the rear target to produce digital signals representing different portions of the optical image as projected to a camera image plane;
   (c) an image correction circuit receiving the digital signals and correcting for spatial distortion of underlying different portions of the optical image captured by the digital signals; and
   (d) combining circuit receiving corrected digital signals from the image correction circuit and combining the digital signals to produce a spatially continuous representation of the optical image.

2. The imaging x-ray detector of claim 1 wherein the different portions of the optical image recorded by the cameras include overlapping portions and wherein the combining circuit applies de-weighting values to the digital signals representing the overlapping portions prior to combining the digital signals.

3. The imaging x-ray detector of claim 2 wherein the rear target is rectangular and including at least four digital cameras directed toward different quadrants of the optical image on the rear target.

4. The imaging x-ray detector of claim 1 wherein the front target receives x-rays across a width and wherein the front target is separated from the camera image plane by an amount no greater than the width.

5. The imaging x-ray detector of claim 4 wherein the front target is rectangular and the width is a measure of the diagonal of the rectangle of the front target.

6. The imaging x-ray detector of claim 1 wherein the front target is circular and the width is a measure of the diameter of the front target.

7. The imaging x-ray detector of claim 1 wherein the digital cameras each includes an optical lens and a solid state light sensitive array coincident with the camera image plane.

8. The imaging x-ray detector of claim 7 wherein the solid state light sensitive array is selected from the group consisting of a charge coupled device, an active pixel device, and a video tube.

9. The imaging x-ray detector of claim 1 wherein the image correction circuit applies a polynomial having predetermined coefficients to the digital signals to correct for spatial distortion of underlying different portions of the optical image.

10. The imaging x-ray detector of claim 1 wherein the electron amplifier is at least one microchannel plate.

11. An imaging x-ray detector comprising:
   (a) an image intensifier having:
      (i) a front target receiving x-rays to eject electrons into an internal volume of the image intensifier,
      (ii) an electron amplifier receiving the ejected electrons to amplify the same; and
      (iii) a rear target receiving the amplified electrons to produce an optical image;
   (b) an imaging array recording an image at an image plane; and
   (c) an image correction circuit storing multiple correction parameters and receiving a mode signal to apply a selected different correction parameters to the digital signal dependant on the mode signal for correcting of spatial distortion of underlying optical image captured in the digital signals.

12. The imaging electronic detector of claim 11 including an orientation sensor for detecting an orientation of the imaging x-ray detector to produce the mode signal;
   whereby orientation related distortion of the image is corrected.

13. The imaging electronic detector of claim 11 further including a lens support positioning at least one lens between the rear target and the imaging array according to the mode signal to project the optical image onto the imaging array at different magnifications associated with the mode signal;
   wherein different spatial distortion associated with different modes may be corrected.

14. The imaging electronic detector of claim 13 wherein the lens support holds multiple lenses different ones of which are positioned between the phosphor target and the image array according to the mode signal.

15. The imaging x-ray detector of claim 11 wherein the front target receives x-rays across a width and wherein the front target is separated from the camera image plane by an amount no greater than the width.

16. The imaging x-ray detector of claim 11 wherein the front target is rectangular and the width is a measure of the diagonal of the rectangle of the front target.

17. The imaging x-ray detector of claim 11 wherein the front target is circular and the width is a measure of the diameter of the front target.

18. The imaging x-ray detector of claim 11 wherein the digital camera includes an optical lens and a solid state light sensitive array coincident with the camera image plane.

19. The imaging x-ray detector of claim 18 wherein the solid state light sensitive array is selected from the group consisting of a charge coupled device, an active pixel device, and a video tube.

20. The imaging x-ray detector of claim 10 wherein the image correction circuit corrects for spatial distortion of underlying different portions of the optical image using a polynomial transformation and wherein the correction parameters are coefficients of the polynomial.

* * * * *